United States Patent
Fay et al.

(10) Patent No.: US 11,589,768 B2
(45) Date of Patent: *Feb. 28, 2023

(54) TISSUE DIAGNOSIS AND TREATMENT USING MINI-ELECTRODES

(71) Applicant: Boston Scientific Scimed Inc., Maple Grove, MN (US)

(72) Inventors: Leon Fay, Lexington, MA (US); Paul Hultz, Brookline, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 672 days.

This patent is subject to a terminal disclaimer.

(21) Appl. No.: 16/733,748

(22) Filed: Jan. 3, 2020

(65) Prior Publication Data

US 2020/0138331 A1 May 7, 2020

Related U.S. Application Data

(63) Continuation of application No. 14/881,112, filed on Oct. 12, 2015, now Pat. No. 10,524,684.

(Continued)

(51) Int. Cl.
*A61B 5/0538* (2021.01)
*A61B 18/14* (2006.01)
(Continued)

(52) U.S. Cl.
CPC ............ *A61B 5/0538* (2013.01); *A61B 5/287* (2021.01); *A61B 18/1492* (2013.01);
(Continued)

(58) Field of Classification Search
CPC ..... A61B 5/0538; A61B 5/287; A61B 5/6852; A61B 18/1492; A61B 2018/00351;
(Continued)

(56) References Cited

U.S. PATENT DOCUMENTS

| | | |
|---|---|---|
| 3,391,845 A | 7/1968 | Bessett |
| 3,773,401 A | 11/1973 | Douklias et al. |

(Continued)

FOREIGN PATENT DOCUMENTS

| | | |
|---|---|---|
| AU | 2014200766 B2 | 6/2015 |
| CA | 2682055 A1 | 10/2008 |

(Continued)

OTHER PUBLICATIONS

Extended European Search Report issued in EP Application 16182627. 6, dated Nov. 8, 2016, 5 pages.

(Continued)

*Primary Examiner* — Eun Hwa Kim
(74) *Attorney, Agent, or Firm* — Nelson Mullins Riley & Scarborough LLP

(57) ABSTRACT

Medical devices and methods for making and using medical devices are disclosed. An example electrophysiology medical device may include a catheter shaft including a distal end portion and a sensing assembly having three or more terminals. The sensing assembly includes one or more current-carrying electrodes and one or more sensing electrodes. The one or more current-carrying electrodes, the one or more sensing electrodes, or both includes a mini-electrode. The mini-electrode is disposed on one of the other electrodes. The medical device may also include a controller coupled to the sensing assembly.

20 Claims, 10 Drawing Sheets

Related U.S. Application Data

(60) Provisional application No. 62/063,296, filed on Oct. 13, 2014.

(51) Int. Cl.
    *A61B 5/287* (2021.01)
    *A61B 5/00* (2006.01)
    *A61B 18/00* (2006.01)
    *A61B 90/00* (2016.01)

(52) U.S. Cl.
    CPC ... *A61B 5/6852* (2013.01); *A61B 2018/00351* (2013.01); *A61B 2018/00357* (2013.01); *A61B 2018/00577* (2013.01); *A61B 2018/00642* (2013.01); *A61B 2018/00827* (2013.01); *A61B 2018/00839* (2013.01); *A61B 2018/00875* (2013.01); *A61B 2018/00892* (2013.01); *A61B 2018/1407* (2013.01); *A61B 2018/1467* (2013.01); *A61B 2018/1497* (2013.01); *A61B 2090/065* (2016.02); *A61B 2562/0257* (2013.01)

(58) Field of Classification Search
    CPC .......... A61B 2018/00357; A61B 2018/00577; A61B 2018/00642; A61B 2018/00827; A61B 2018/00839; A61B 2018/00875; A61B 2018/00892; A61B 2018/1407; A61B 2018/1467; A61B 2018/1497; A61B 2090/065; A61B 2562/0257
    See application file for complete search history.

(56) References Cited

U.S. PATENT DOCUMENTS

| | | |
|---|---|---|
| 4,466,443 A | 8/1984 | Utsugi |
| 4,602,624 A | 7/1986 | Naples et al. |
| 4,633,882 A | 1/1987 | Matsuo et al. |
| 4,732,149 A | 3/1988 | Sutter |
| 4,745,928 A | 5/1988 | Webler et al. |
| 4,763,660 A | 8/1988 | Kroll et al. |
| 4,945,912 A | 8/1990 | Langberg |
| 4,966,145 A | 10/1990 | Kikumoto et al. |
| 5,019,076 A | 5/1991 | Yamanashi et al. |
| 5,029,588 A | 7/1991 | Yock et al. |
| 5,114,423 A | 5/1992 | Kasprzyk et al. |
| 5,151,100 A | 9/1992 | Abele et al. |
| 5,178,150 A | 1/1993 | Silverstein et al. |
| 5,217,460 A | 6/1993 | Knoepfler |
| 5,230,349 A | 7/1993 | Langberg |
| 5,238,004 A | 8/1993 | Sahatjian et al. |
| 5,240,003 A | 8/1993 | Lancee et al. |
| 5,242,441 A | 9/1993 | Avitall |
| 5,254,088 A | 10/1993 | Lundquist et al. |
| 5,277,201 A | 1/1994 | Stern |
| 5,295,482 A | 3/1994 | Clare et al. |
| 5,318,589 A | 6/1994 | Lichtman |
| 5,324,284 A | 6/1994 | Imran |
| 5,331,966 A | 7/1994 | Bennett et al. |
| 5,334,193 A | 8/1994 | Nardella |
| 5,341,807 A | 8/1994 | Nardella |
| 5,377,685 A | 1/1995 | Kazi et al. |
| 5,383,874 A | 1/1995 | Jackson et al. |
| 5,385,146 A | 1/1995 | Goldreyer |
| 5,385,148 A | 1/1995 | Lesh et al. |
| 5,391,199 A | 2/1995 | Ben-Haim |
| 5,398,683 A | 3/1995 | Edwards et al. |
| 5,415,654 A | 5/1995 | Daikuzono |
| 5,417,689 A | 5/1995 | Fine |
| 5,423,811 A | 6/1995 | Imran et al. |
| 5,447,529 A | 9/1995 | Marchlinski et al. |
| 5,456,682 A | 10/1995 | Edwards et al. |
| 5,462,521 A | 10/1995 | Brucker et al. |
| 5,482,054 A | 1/1996 | Slater et al. |
| 5,485,849 A | 1/1996 | Panescu et al. |
| 5,494,042 A | 2/1996 | Panescu et al. |
| 5,500,012 A | 3/1996 | Brucker et al. |
| 5,520,683 A | 5/1996 | Subramaniam et al. |
| 5,545,161 A | 8/1996 | Imran |
| 5,571,088 A | 11/1996 | Lennox et al. |
| 5,573,535 A | 11/1996 | Viklund |
| 5,575,772 A | 11/1996 | Lennox |
| 5,579,764 A | 12/1996 | Goldreyer |
| 5,582,609 A | 12/1996 | Swanson et al. |
| 5,643,197 A | 7/1997 | Brucker et al. |
| 5,647,870 A | 7/1997 | Kordis et al. |
| 5,676,693 A | 10/1997 | LaFontaine |
| 5,688,267 A | 11/1997 | Panescu et al. |
| 5,718,701 A | 2/1998 | Shai et al. |
| 5,722,402 A | 3/1998 | Swanson et al. |
| 5,735,846 A | 4/1998 | Panescu et al. |
| 5,762,067 A | 6/1998 | Dunham et al. |
| 5,788,636 A | 8/1998 | Curley |
| 5,792,064 A | 8/1998 | Panescu et al. |
| 5,800,482 A | 9/1998 | Pomeranz et al. |
| 5,810,802 A | 9/1998 | Panescu et al. |
| 5,820,568 A | 10/1998 | Willis |
| 5,830,213 A | 11/1998 | Panescu et al. |
| 5,833,621 A | 11/1998 | Panescu et al. |
| 5,836,875 A | 11/1998 | Webster, Jr. |
| 5,836,990 A | 11/1998 | Li |
| 5,868,735 A | 2/1999 | Lafontaine |
| 5,871,483 A | 2/1999 | Jackson et al. |
| 5,871,526 A | 2/1999 | Gibbs et al. |
| 5,876,336 A | 3/1999 | Swanson et al. |
| 5,885,278 A | 3/1999 | Fleischman |
| 5,893,847 A | 4/1999 | Kordis |
| 5,913,854 A | 6/1999 | Maguire et al. |
| 5,913,856 A | 6/1999 | Chia et al. |
| 5,916,213 A | 6/1999 | Haissaguerre et al. |
| 5,919,188 A | 7/1999 | Shearon et al. |
| 5,957,850 A | 9/1999 | Marian et al. |
| 6,002,968 A | 12/1999 | Edwards |
| 6,004,269 A | 12/1999 | Crowley et al. |
| 6,006,755 A | 12/1999 | Edwards |
| 6,027,500 A | 2/2000 | Buckles et al. |
| 6,030,379 A | 2/2000 | Panescu et al. |
| 6,042,559 A | 3/2000 | Dobak, III |
| 6,050,267 A | 4/2000 | Nardella et al. |
| 6,050,994 A | 4/2000 | Sherman |
| 6,059,778 A | 5/2000 | Sherman |
| 6,063,078 A | 5/2000 | Wittkampf |
| 6,064,905 A | 5/2000 | Webster et al. |
| 6,068,629 A | 5/2000 | Haissaguerre et al. |
| 6,070,094 A | 5/2000 | Swanson et al. |
| 6,071,281 A | 6/2000 | Burnside et al. |
| 6,083,170 A | 7/2000 | Ben-Haim |
| 6,083,222 A | 7/2000 | Klein et al. |
| 6,099,524 A | 8/2000 | Lipson et al. |
| 6,101,409 A | 8/2000 | Swanson et al. |
| 6,116,027 A | 9/2000 | Smith et al. |
| 6,120,476 A | 9/2000 | Fung et al. |
| 6,162,184 A | 12/2000 | Swanson et al. |
| 6,165,123 A | 12/2000 | Thompson |
| 6,171,275 B1 | 1/2001 | Webster, Jr. |
| 6,171,305 B1 | 1/2001 | Sherman |
| 6,200,314 B1 | 3/2001 | Sherman |
| 6,206,831 B1 | 3/2001 | Suorsa et al. |
| 6,210,337 B1 | 4/2001 | Dunham et al. |
| 6,216,027 B1 | 4/2001 | Willis et al. |
| 6,224,557 B1 | 5/2001 | Ziel et al. |
| 6,233,491 B1 | 5/2001 | Kordis et al. |
| 6,241,724 B1 | 6/2001 | Fleischman et al. |
| 6,241,754 B1 | 6/2001 | Swanson et al. |
| 6,258,087 B1 | 7/2001 | Edwards et al. |
| 6,270,493 B1 | 8/2001 | Lalonde et al. |
| 6,290,697 B1 | 9/2001 | Tu et al. |
| 6,352,534 B1 | 3/2002 | Paddock et al. |
| 6,395,325 B1 | 5/2002 | Hedge et al. |
| 6,400,981 B1 | 6/2002 | Govari |
| 6,423,002 B1 | 7/2002 | Hossack |
| 6,475,213 B1 | 11/2002 | Swanson et al. |
| 6,488,678 B2 | 12/2002 | Sherman |

(56) References Cited

U.S. PATENT DOCUMENTS

| | | |
|---|---|---|
| 6,491,710 B2 | 12/2002 | Satake |
| 6,500,174 B1 | 12/2002 | Maguire et al. |
| 6,508,767 B2 | 1/2003 | Burns et al. |
| 6,508,769 B2 | 1/2003 | Bonnefous |
| 6,508,803 B1 | 1/2003 | Horikawa et al. |
| 6,514,249 B1 | 2/2003 | Maguire et al. |
| 6,516,667 B1 | 2/2003 | Broad et al. |
| 6,517,533 B1 | 2/2003 | Swaminathan |
| 6,517,534 B1 | 2/2003 | McGovern et al. |
| 6,537,271 B1 | 3/2003 | Murray et al. |
| 6,544,175 B1 | 4/2003 | Newman |
| 6,546,270 B1 | 4/2003 | Goldin et al. |
| 6,547,788 B1 | 4/2003 | Maguire et al. |
| 6,569,160 B1 | 5/2003 | Goldin et al. |
| 6,569,162 B2 | 5/2003 | He |
| 6,572,547 B2 | 6/2003 | Miller et al. |
| 6,575,966 B2 | 6/2003 | Lane et al. |
| 6,575,969 B1 | 6/2003 | Rittman et al. |
| 6,579,278 B1 | 6/2003 | Bencini |
| 6,582,372 B2 | 6/2003 | Poland |
| 6,584,345 B2 | 6/2003 | Govari |
| 6,589,182 B1 | 7/2003 | Loftman et al. |
| 6,589,238 B2 | 7/2003 | Edwards et al. |
| 6,592,525 B2 | 7/2003 | Miller et al. |
| 6,602,242 B1 | 8/2003 | Fung et al. |
| 6,620,103 B1 | 9/2003 | Bruce et al. |
| 6,632,179 B2 | 10/2003 | Wilson et al. |
| 6,638,222 B2 | 10/2003 | Chandrasekaran et al. |
| 6,640,120 B1 | 10/2003 | Swanson et al. |
| 6,647,281 B2 | 11/2003 | Morency |
| 6,656,174 B1 | 12/2003 | Hegde et al. |
| 6,658,279 B2 | 12/2003 | Swanson et al. |
| 6,663,573 B2 | 12/2003 | Goldin |
| 6,663,622 B1 | 12/2003 | Foley et al. |
| 6,666,862 B2 | 12/2003 | Jain et al. |
| 6,673,067 B1 | 1/2004 | Peyman |
| 6,676,606 B2 | 1/2004 | Simpson et al. |
| 6,692,441 B1 | 2/2004 | Poland et al. |
| 6,705,992 B2 | 3/2004 | Gatzke |
| 6,709,396 B2 | 3/2004 | Flesch et al. |
| 6,711,429 B1 | 3/2004 | Gilboa et al. |
| 6,719,756 B1 | 4/2004 | Muntermann |
| 6,723,094 B1 | 4/2004 | Desinger |
| 6,735,465 B2 | 5/2004 | Panescu |
| 6,736,814 B2 | 5/2004 | Manna et al. |
| 6,743,174 B2 | 6/2004 | Ng et al. |
| 6,773,402 B2 | 8/2004 | Govari et al. |
| 6,776,758 B2 | 8/2004 | Peszynski et al. |
| 6,796,979 B2 | 9/2004 | Lentz |
| 6,796,980 B2 | 9/2004 | Hall |
| 6,804,545 B2 | 10/2004 | Fuimaono et al. |
| 6,811,550 B2 | 11/2004 | Holland et al. |
| 6,824,517 B2 | 11/2004 | Salgo et al. |
| 6,837,884 B2 | 1/2005 | Woloszko |
| 6,845,257 B2 | 1/2005 | Fuimaono et al. |
| 6,845,264 B1 | 1/2005 | Skladnev et al. |
| 6,917,834 B2 | 7/2005 | Koblish et al. |
| 6,922,579 B2 | 7/2005 | Taimisto et al. |
| 6,923,808 B2 | 8/2005 | Taimisto |
| 6,932,811 B2 | 8/2005 | Hooven et al. |
| 6,945,938 B2 | 9/2005 | Grunwald |
| 6,950,689 B1 | 9/2005 | Willis et al. |
| 6,952,615 B2 | 10/2005 | Satake |
| 6,958,040 B2 | 10/2005 | Oliver et al. |
| 6,972,016 B2 | 12/2005 | Hill et al. |
| 7,001,383 B2 | 2/2006 | Keidar |
| 7,037,264 B2 | 5/2006 | Poland |
| 7,047,068 B2 | 5/2006 | Haissaguerre |
| 7,097,643 B2 | 8/2006 | Cornelius et al. |
| 7,099,711 B2 | 8/2006 | Fuimaono et al. |
| 7,105,122 B2 | 9/2006 | Karason |
| 7,112,198 B2 | 9/2006 | Satake |
| 7,115,122 B1 | 10/2006 | Swanson et al. |
| 7,123,951 B2 | 10/2006 | Fuimaono et al. |
| 7,125,409 B2 | 10/2006 | Truckai et al. |
| 7,131,947 B2 | 11/2006 | Demers |
| 7,166,075 B2 | 1/2007 | Varghese et al. |
| 7,181,262 B2 | 2/2007 | Fuimaono et al. |
| 7,198,625 B1 | 4/2007 | Hui et al. |
| 7,220,233 B2 | 5/2007 | Nita et al. |
| 7,232,433 B1 | 6/2007 | Schlesinger et al. |
| 7,247,155 B2 | 7/2007 | Hoey et al. |
| 7,270,634 B2 | 9/2007 | Scampini et al. |
| 7,288,088 B2 | 10/2007 | Swanson |
| 7,291,142 B2 | 11/2007 | Eberl et al. |
| 7,306,561 B2 | 12/2007 | Sathyanarayana |
| 7,335,052 B2 | 2/2008 | D Sa |
| 7,347,820 B2 | 3/2008 | Bonnefous |
| 7,347,821 B2 | 3/2008 | Skyba et al. |
| 7,347,857 B2 | 3/2008 | Anderson et al. |
| 7,361,144 B2 | 4/2008 | Levrier et al. |
| 7,422,591 B2 | 9/2008 | Phan |
| 7,438,714 B2 | 10/2008 | Phan |
| 7,455,669 B2 | 11/2008 | Swanson |
| 7,488,289 B2 | 2/2009 | Suorsa et al. |
| 7,507,205 B2 | 3/2009 | Borovsky et al. |
| 7,507,237 B2 | 3/2009 | Geistert |
| 7,519,410 B2 | 4/2009 | Taimisto et al. |
| 7,529,393 B2 | 5/2009 | Peszynski et al. |
| 7,534,207 B2 | 5/2009 | Shehada et al. |
| 7,544,164 B2 | 6/2009 | Knowles et al. |
| 7,549,988 B2 | 6/2009 | Eberl et al. |
| 7,569,052 B2 | 8/2009 | Phan et al. |
| 7,578,791 B2 | 8/2009 | Rafter |
| 7,582,083 B2 | 9/2009 | Swanson |
| 7,585,310 B2 | 9/2009 | Phan et al. |
| 7,610,073 B2 | 10/2009 | Fuimaono et al. |
| 7,648,462 B2 | 1/2010 | Jenkins et al. |
| 7,697,972 B2 | 4/2010 | Verard et al. |
| 7,704,208 B2 | 4/2010 | Thiele |
| 7,720,420 B2 | 5/2010 | Kajita |
| 7,727,231 B2 | 6/2010 | Swanson |
| 7,736,362 B2 | 6/2010 | Eberl et al. |
| 7,740,629 B2 | 6/2010 | Anderson et al. |
| 7,758,508 B1 | 7/2010 | Thiele et al. |
| 7,766,833 B2 | 8/2010 | Lee et al. |
| 7,776,033 B2 | 8/2010 | Swanson |
| 7,785,324 B2 | 8/2010 | Eberl |
| 7,794,398 B2 | 9/2010 | Salgo |
| 7,796,789 B2 | 9/2010 | Salgo et al. |
| 7,799,025 B2 | 9/2010 | Wellman |
| 7,815,572 B2 | 10/2010 | Loupas |
| 7,819,863 B2 | 10/2010 | Eggers et al. |
| 7,837,624 B1 | 11/2010 | Hossack et al. |
| 7,859,170 B2 | 12/2010 | Knowles et al. |
| 7,862,561 B2 | 1/2011 | Swanson et al. |
| 7,862,562 B2 | 1/2011 | Eberl |
| 7,879,029 B2 | 2/2011 | Jimenez |
| 7,892,228 B2 | 2/2011 | Landis et al. |
| 7,894,871 B2 | 2/2011 | Wittkampf et al. |
| 7,918,850 B2 | 4/2011 | Govari et al. |
| 7,957,817 B1 | 6/2011 | Gillespie et al. |
| 7,996,085 B2 | 8/2011 | Levin |
| 8,016,822 B2 | 9/2011 | Swanson |
| 8,048,028 B2 | 11/2011 | Horn et al. |
| 8,103,327 B2 | 1/2012 | Harlev et al. |
| 8,128,617 B2 | 3/2012 | Bencini et al. |
| 8,160,690 B2 | 4/2012 | Wilfley et al. |
| 8,162,935 B2 | 4/2012 | Paul et al. |
| 8,183,441 B2 | 5/2012 | Cukadar |
| 8,265,745 B2 | 9/2012 | Hauck et al. |
| 8,267,926 B2 | 9/2012 | Paul et al. |
| 8,290,578 B2 | 10/2012 | Schneider |
| 8,317,783 B2 | 11/2012 | Cao et al. |
| 8,369,922 B2 | 2/2013 | Paul et al. |
| 8,400,164 B2 | 3/2013 | Osadchy et al. |
| 8,403,925 B2 | 3/2013 | Miller et al. |
| 8,406,866 B2 | 3/2013 | Deno et al. |
| 8,414,579 B2 | 4/2013 | Kim et al. |
| 8,449,535 B2 | 5/2013 | Deno et al. |
| 8,454,538 B2 | 6/2013 | Wittkampf et al. |
| 8,454,589 B2 | 6/2013 | Deno et al. |
| 8,489,184 B2 | 7/2013 | Wilfley et al. |
| 8,579,889 B2 | 11/2013 | Bencini |

(56) References Cited

U.S. PATENT DOCUMENTS

| | | |
|---|---|---|
| 8,583,215 B2 | 11/2013 | Lichtenstein |
| 8,603,084 B2 | 12/2013 | Fish et al. |
| 8,603,085 B2 | 12/2013 | Jimenez |
| 8,644,950 B2 | 2/2014 | Hauck |
| 8,657,814 B2 | 2/2014 | Werneth et al. |
| 8,672,936 B2 | 3/2014 | Thao et al. |
| 8,679,109 B2 | 3/2014 | Paul et al. |
| 8,728,077 B2 | 5/2014 | Paul et al. |
| 8,740,900 B2 | 6/2014 | Kim et al. |
| 8,755,860 B2 | 6/2014 | Paul et al. |
| 8,771,343 B2 | 7/2014 | Weber et al. |
| 8,876,817 B2 | 11/2014 | Avitall et al. |
| 8,894,643 B2 | 11/2014 | Watson et al. |
| 8,906,011 B2 | 12/2014 | Gelbart et al. |
| 8,945,015 B2 | 2/2015 | Rankin et al. |
| 8,945,117 B2 | 2/2015 | Bencini |
| 8,998,890 B2 | 4/2015 | Paul et al. |
| 9,044,300 B2 | 6/2015 | Belhe et al. |
| 9,089,340 B2 | 7/2015 | Hastings et al. |
| 9,125,565 B2 | 9/2015 | Hauck |
| 9,125,668 B2 | 9/2015 | Subramaniam et al. |
| 9,168,004 B2 | 10/2015 | Gliner et al. |
| 9,173,586 B2 | 11/2015 | Deno et al. |
| 9,211,156 B2 | 12/2015 | Kim et al. |
| 9,241,687 B2 | 1/2016 | McGee |
| 9,241,761 B2 | 1/2016 | Rankin et al. |
| 9,254,163 B2 | 2/2016 | Paul et al. |
| 9,265,434 B2 | 2/2016 | Merschon et al. |
| 9,271,782 B2 | 3/2016 | Paul et al. |
| 9,283,026 B2 | 3/2016 | Paul et al. |
| 9,370,329 B2 | 6/2016 | Tun et al. |
| 9,393,072 B2 | 7/2016 | Kim et al. |
| 9,463,064 B2 | 10/2016 | Subramaniam et al. |
| 9,603,659 B2 | 3/2017 | Subramaniam et al. |
| 9,622,897 B1 | 4/2017 | Stangenes et al. |
| 9,743,854 B2 | 8/2017 | Stewart et al. |
| 9,757,191 B2 | 9/2017 | Avitall et al. |
| 9,956,035 B2 | 5/2018 | Govari et al. |
| 10,524,684 B2 | 1/2020 | Fay et al. |
| 2001/0008967 A1 | 7/2001 | Sherman |
| 2001/0029371 A1 | 10/2001 | Kordis |
| 2001/0031921 A1 | 10/2001 | Bonnefous |
| 2001/0034518 A1 | 10/2001 | Edwards et al. |
| 2001/0039381 A1 | 11/2001 | Burns et al. |
| 2002/0007180 A1 | 1/2002 | Wittenberger et al. |
| 2002/0045893 A1 | 4/2002 | Lane et al. |
| 2002/0065512 A1 | 5/2002 | Fjield et al. |
| 2002/0072663 A1 | 6/2002 | Fuimaono et al. |
| 2002/0082503 A1 | 6/2002 | Chandrasekaran et al. |
| 2002/0087208 A1 | 7/2002 | Koblish et al. |
| 2002/0091384 A1 | 7/2002 | Hooven et al. |
| 2002/0107447 A1 | 8/2002 | Suorsa et al. |
| 2002/0111548 A1 | 8/2002 | Swanson et al. |
| 2002/0147391 A1 | 10/2002 | Morency |
| 2002/0151807 A1 | 10/2002 | Goldin |
| 2002/0161306 A1 | 10/2002 | Govari |
| 2002/0165448 A1 | 11/2002 | Ben-Haim et al. |
| 2002/0169445 A1 | 11/2002 | Jain et al. |
| 2002/0183731 A1 | 12/2002 | Holland et al. |
| 2002/0183735 A1 | 12/2002 | Edwards et al. |
| 2002/0198521 A1 | 12/2002 | Maguire |
| 2003/0004505 A1 | 1/2003 | Bencini et al. |
| 2003/0004506 A1 | 1/2003 | Messing |
| 2003/0013955 A1 | 1/2003 | Poland |
| 2003/0013958 A1 | 1/2003 | Govari et al. |
| 2003/0014051 A1 | 1/2003 | Woloszko |
| 2003/0014095 A1 | 1/2003 | Kramer et al. |
| 2003/0028103 A1 | 2/2003 | Miller et al. |
| 2003/0028104 A1 | 2/2003 | Wilson et al. |
| 2003/0040804 A1 | 2/2003 | Stack et al. |
| 2003/0065371 A1 | 4/2003 | Satake |
| 2003/0078509 A1 | 4/2003 | Panescu |
| 2003/0088240 A1 | 5/2003 | Saadat |
| 2003/0092993 A1 | 5/2003 | Grunwald |
| 2003/0097125 A1 | 5/2003 | Hall |
| 2003/0158548 A1 | 8/2003 | Phan et al. |
| 2003/0158549 A1 | 8/2003 | Swanson |
| 2003/0163045 A1 | 8/2003 | Gatzke |
| 2003/0163130 A1 | 8/2003 | Manna et al. |
| 2003/0171672 A1 | 9/2003 | Varghese et al. |
| 2003/0187353 A1 | 10/2003 | Ng et al. |
| 2003/0191380 A1 | 10/2003 | Fuimaono et al. |
| 2003/0195407 A1 | 10/2003 | Fuimaono et al. |
| 2003/0208124 A1 | 11/2003 | Poland |
| 2003/0229285 A1 | 12/2003 | Simpson et al. |
| 2003/0229286 A1 | 12/2003 | Lenker |
| 2003/0236462 A1 | 12/2003 | Salgo et al. |
| 2004/0006268 A1 | 1/2004 | Gilboa et al. |
| 2004/0010200 A1 | 1/2004 | Sweeney |
| 2004/0015084 A1 | 1/2004 | Flesch et al. |
| 2004/0073114 A1 | 4/2004 | Oliver et al. |
| 2004/0073118 A1 | 4/2004 | Peszynski et al. |
| 2004/0078036 A1 | 4/2004 | Keidar |
| 2004/0082860 A1 | 4/2004 | Haissaguerre |
| 2004/0092806 A1 | 5/2004 | Sagon et al. |
| 2004/0097805 A1 | 5/2004 | Verard et al. |
| 2004/0116793 A1 | 6/2004 | Taimisto et al. |
| 2004/0116916 A1 | 6/2004 | Lentz |
| 2004/0137098 A1 | 7/2004 | Karason |
| 2004/0147920 A1 | 7/2004 | Keidar |
| 2004/0158139 A1 | 8/2004 | Fuimaono et al. |
| 2004/0158140 A1 | 8/2004 | Fuimaono et al. |
| 2004/0158238 A1 | 8/2004 | Lalonde et al. |
| 2004/0158270 A1 | 8/2004 | Wyzgala et al. |
| 2004/0162556 A1 | 8/2004 | Swanson |
| 2004/0167509 A1 | 8/2004 | Taimisto |
| 2004/0172110 A1 | 9/2004 | Satake |
| 2004/0186467 A1 | 9/2004 | Swanson et al. |
| 2004/0193042 A1 | 9/2004 | Scampini et al. |
| 2004/0204670 A1 | 10/2004 | Nita et al. |
| 2004/0210136 A1 | 10/2004 | Varghese et al. |
| 2004/0215177 A1 | 10/2004 | Swanson |
| 2004/0215183 A1 | 10/2004 | Hoey et al. |
| 2004/0215186 A1 | 10/2004 | Cornelius et al. |
| 2004/0225219 A1 | 11/2004 | Demers |
| 2004/0236192 A1 | 11/2004 | Necola et al. |
| 2004/0267125 A1 | 12/2004 | Skyba et al. |
| 2005/0033331 A1 | 2/2005 | Burnett et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0065508 A1 | 3/2005 | Johnson et al. |
| 2005/0070894 A1 | 3/2005 | McClurken |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0124899 A1 | 6/2005 | Byrd et al. |
| 2005/0125020 A1 | 6/2005 | Meade et al. |
| 2005/0165391 A1 | 7/2005 | Maguire et al. |
| 2005/0187544 A1 | 8/2005 | Swanson et al. |
| 2005/0203505 A1 | 9/2005 | Megerman et al. |
| 2005/0203597 A1 | 9/2005 | Yamazaki et al. |
| 2005/0215993 A1 | 9/2005 | Phan |
| 2005/0228286 A1 | 10/2005 | Messerly et al. |
| 2005/0228290 A1 | 10/2005 | Borovsky et al. |
| 2005/0228504 A1 | 10/2005 | Demarais |
| 2005/0251121 A1 | 11/2005 | Swanson |
| 2005/0251122 A1 | 11/2005 | Swanson |
| 2005/0251123 A1 | 11/2005 | Eberl et al. |
| 2005/0273060 A1 | 12/2005 | Levy et al. |
| 2005/0288667 A1 | 12/2005 | Thompson et al. |
| 2006/0030919 A1 | 2/2006 | Mrva et al. |
| 2006/0047277 A1 | 3/2006 | Eberl et al. |
| 2006/0052698 A1 | 3/2006 | Loupas |
| 2006/0058657 A1 | 3/2006 | Sathyanarayana |
| 2006/0058668 A1 | 3/2006 | Levrier et al. |
| 2006/0074309 A1 | 4/2006 | Bonnefous |
| 2006/0089634 A1 | 4/2006 | Anderson et al. |

(56) References Cited

U.S. PATENT DOCUMENTS

| | | |
|---|---|---|
| 2006/0100522 A1 | 5/2006 | Yuan et al. |
| 2006/0155272 A1 | 7/2006 | Swanson |
| 2006/0155273 A1 | 7/2006 | Swanson |
| 2006/0155274 A1 | 7/2006 | Swanson et al. |
| 2006/0161146 A1 | 7/2006 | Cornelius et al. |
| 2006/0161201 A1 | 7/2006 | Phan et al. |
| 2006/0182320 A1 | 8/2006 | Peszynski et al. |
| 2006/0184112 A1 | 8/2006 | Horn et al. |
| 2006/0193504 A1 | 8/2006 | Salgo et al. |
| 2006/0195079 A1 | 8/2006 | Eberl |
| 2006/0195080 A1 | 8/2006 | Ebert |
| 2006/0195081 A1 | 8/2006 | Landis et al. |
| 2006/0206109 A1 | 9/2006 | Swanson |
| 2006/0224153 A1 | 10/2006 | Fischell et al. |
| 2006/0247607 A1 | 11/2006 | Cornelius et al. |
| 2006/0247683 A1 | 11/2006 | Danek et al. |
| 2006/0253028 A1 | 11/2006 | Lam et al. |
| 2006/0253116 A1 | 11/2006 | Avitall et al. |
| 2006/0258940 A1 | 11/2006 | D Sa |
| 2006/0271032 A1 | 11/2006 | Chin et al. |
| 2006/0271034 A1 | 11/2006 | Swanson |
| 2007/0003811 A1 | 1/2007 | Zerfass et al. |
| 2007/0016019 A1 | 1/2007 | Salgo |
| 2007/0016054 A1 | 1/2007 | Cao et al. |
| 2007/0016059 A1 | 1/2007 | Morimoto et al. |
| 2007/0016228 A1 | 1/2007 | Salas |
| 2007/0021744 A1 | 1/2007 | Creighton, IV |
| 2007/0032724 A1 | 2/2007 | Thiele |
| 2007/0049925 A1 | 3/2007 | Phan et al. |
| 2007/0055225 A1 | 3/2007 | Dodd et al. |
| 2007/0073135 A1 | 3/2007 | Lee et al. |
| 2007/0083193 A1 | 4/2007 | Werneth et al. |
| 2007/0088345 A1 | 4/2007 | Larson et al. |
| 2007/0123764 A1 | 5/2007 | Thao et al. |
| 2007/0129633 A1 | 6/2007 | Lee et al. |
| 2007/0135700 A1 | 6/2007 | Taimisto et al. |
| 2007/0156128 A1 | 7/2007 | Jimenez |
| 2007/0165916 A1 | 7/2007 | Cloutier et al. |
| 2007/0167813 A1 | 7/2007 | Lee et al. |
| 2007/0179375 A1 | 8/2007 | Fuimaono et al. |
| 2007/0181139 A1 | 8/2007 | Hauck |
| 2007/0198007 A1 | 8/2007 | Govari et al. |
| 2007/0225610 A1 | 9/2007 | Mickley et al. |
| 2007/0238997 A1 | 10/2007 | Camus |
| 2007/0239017 A1 | 10/2007 | Knowles et al. |
| 2007/0270791 A1 | 11/2007 | Wang et al. |
| 2007/0270794 A1 | 11/2007 | Anderson et al. |
| 2007/0276239 A1 | 11/2007 | Rafter |
| 2008/0004691 A1 | 1/2008 | Weber et al. |
| 2008/0009733 A1 | 1/2008 | Saksena |
| 2008/0015568 A1 | 1/2008 | Paul et al. |
| 2008/0025145 A1 | 1/2008 | Peszynski et al. |
| 2008/0051841 A1 | 2/2008 | Swerdlow et al. |
| 2008/0056750 A1 | 3/2008 | Kajita |
| 2008/0058836 A1 | 3/2008 | Moll et al. |
| 2008/0086073 A1 | 4/2008 | McDaniel |
| 2008/0091109 A1 | 4/2008 | Abraham |
| 2008/0140065 A1 | 6/2008 | Rioux et al. |
| 2008/0147060 A1 | 6/2008 | Choi |
| 2008/0161668 A1 | 7/2008 | Wittkampf et al. |
| 2008/0161705 A1 | 7/2008 | Podmore et al. |
| 2008/0161795 A1 | 7/2008 | Wang et al. |
| 2008/0161796 A1 | 7/2008 | Cao et al. |
| 2008/0195089 A1 | 8/2008 | Thiagalingam et al. |
| 2008/0228111 A1 | 9/2008 | Nita |
| 2008/0243214 A1* | 10/2008 | Koblish ............. A61B 18/1492 606/41 |
| 2008/0249518 A1 | 10/2008 | Warnking et al. |
| 2008/0255470 A1 | 10/2008 | Hauck et al. |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0281322 A1 | 11/2008 | Sherman et al. |
| 2008/0287803 A1 | 11/2008 | Li et al. |
| 2008/0288038 A1 | 11/2008 | Paul et al. |
| 2008/0300454 A1 | 12/2008 | Goto |
| 2008/0300589 A1 | 12/2008 | Paul et al. |
| 2008/0312521 A1 | 12/2008 | Solomon |
| 2008/0312713 A1 | 12/2008 | Wilfley et al. |
| 2009/0000383 A1 | 1/2009 | Knowles et al. |
| 2009/0005771 A1 | 1/2009 | Lieber et al. |
| 2009/0024119 A1 | 1/2009 | Wellman |
| 2009/0030312 A1 | 1/2009 | Hadjicostis |
| 2009/0048591 A1 | 2/2009 | Ibrahim et al. |
| 2009/0056344 A1 | 3/2009 | Poch |
| 2009/0062790 A1 | 3/2009 | Malchano et al. |
| 2009/0062795 A1 | 3/2009 | Vakharia et al. |
| 2009/0069807 A1 | 3/2009 | Eggers et al. |
| 2009/0076390 A1 | 3/2009 | Lee et al. |
| 2009/0088631 A1 | 4/2009 | Dietz et al. |
| 2009/0093810 A1 | 4/2009 | Subramaniam et al. |
| 2009/0093811 A1 | 4/2009 | Koblish et al. |
| 2009/0099472 A1 | 4/2009 | Remmert et al. |
| 2009/0131930 A1 | 5/2009 | Gelbart et al. |
| 2009/0131932 A1 | 5/2009 | Vakharia et al. |
| 2009/0163904 A1 | 6/2009 | Miller et al. |
| 2009/0171235 A1 | 7/2009 | Schneider et al. |
| 2009/0171274 A1 | 7/2009 | Harlev et al. |
| 2009/0171341 A1 | 7/2009 | Pope et al. |
| 2009/0171345 A1 | 7/2009 | Miller et al. |
| 2009/0177069 A1 | 7/2009 | Razavi |
| 2009/0177111 A1 | 7/2009 | Miller et al. |
| 2009/0182316 A1 | 7/2009 | Bencini |
| 2009/0209950 A1 | 8/2009 | Starksen |
| 2009/0216125 A1 | 8/2009 | Lenker |
| 2009/0240247 A1 | 9/2009 | Rioux et al. |
| 2009/0259274 A1 | 10/2009 | Simon et al. |
| 2009/0275827 A1 | 11/2009 | Aiken et al. |
| 2009/0281541 A1 | 11/2009 | Ibrahim et al. |
| 2009/0287202 A1 | 11/2009 | Ingle et al. |
| 2009/0292209 A1 | 11/2009 | Hadjicostis |
| 2009/0299355 A1 | 12/2009 | Bencini et al. |
| 2009/0299360 A1 | 12/2009 | Ormsby |
| 2009/0306643 A1 | 12/2009 | Pappone et al. |
| 2010/0010487 A1 | 1/2010 | Phan et al. |
| 2010/0030204 A1 | 2/2010 | Stein et al. |
| 2010/0057072 A1 | 3/2010 | Roman et al. |
| 2010/0069921 A1 | 3/2010 | Miller et al. |
| 2010/0076402 A1 | 3/2010 | Mazzone et al. |
| 2010/0076426 A1 | 3/2010 | De et al. |
| 2010/0094274 A1 | 4/2010 | Narayan et al. |
| 2010/0106155 A1 | 4/2010 | Anderson et al. |
| 2010/0113938 A1 | 5/2010 | Park et al. |
| 2010/0114092 A1 | 5/2010 | Eisele et al. |
| 2010/0117659 A1 | 5/2010 | Osadchy et al. |
| 2010/0121393 A1 | 5/2010 | Levin |
| 2010/0137944 A1* | 6/2010 | Zhu ............. A61B 5/063 607/59 |
| 2010/0145221 A1 | 6/2010 | Brunnett et al. |
| 2010/0152728 A1 | 6/2010 | Park et al. |
| 2010/0168557 A1 | 7/2010 | Deno et al. |
| 2010/0168568 A1 | 7/2010 | Sliwa |
| 2010/0168570 A1 | 7/2010 | Sliwa et al. |
| 2010/0168735 A1 | 7/2010 | Deno et al. |
| 2010/0168831 A1 | 7/2010 | Korivi et al. |
| 2010/0228247 A1 | 9/2010 | Paul et al. |
| 2010/0241117 A1 | 9/2010 | Paul et al. |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0262140 A1 | 10/2010 | Watson et al. |
| 2010/0268217 A1 | 10/2010 | Habib |
| 2010/0286690 A1 | 11/2010 | Paul et al. |
| 2010/0298823 A1 | 11/2010 | Cao et al. |
| 2010/0298826 A1 | 11/2010 | Leo et al. |
| 2010/0331658 A1 | 12/2010 | Kim et al. |
| 2011/0028820 A1 | 2/2011 | Lau et al. |
| 2011/0034915 A1 | 2/2011 | Ibrahim et al. |
| 2011/0071400 A1 | 3/2011 | Hastings et al. |
| 2011/0071401 A1 | 3/2011 | Hastings et al. |
| 2011/0106075 A1 | 5/2011 | Jimenez |
| 2011/0112569 A1 | 5/2011 | Friedman et al. |
| 2011/0118727 A1 | 5/2011 | Fish et al. |

(56) References Cited

U.S. PATENT DOCUMENTS

| | | |
|---|---|---|
| 2011/0125008 A1 | 5/2011 | Wittkampf et al. |
| 2011/0125143 A1 | 5/2011 | Gross et al. |
| 2011/0125150 A1 | 5/2011 | Deno et al. |
| 2011/0130648 A1 | 6/2011 | Beeckler et al. |
| 2011/0137151 A1 | 6/2011 | Lichtenstein |
| 2011/0137153 A1 | 6/2011 | Govari et al. |
| 2011/0144491 A1 | 6/2011 | Sliwa et al. |
| 2011/0144524 A1 | 6/2011 | Fish et al. |
| 2011/0160584 A1 | 6/2011 | Paul et al. |
| 2011/0237933 A1 | 9/2011 | Cohen |
| 2011/0282249 A1 | 11/2011 | Tsoref et al. |
| 2011/0319782 A1 | 12/2011 | Sweeney et al. |
| 2012/0004547 A1 | 1/2012 | Harks et al. |
| 2012/0004621 A1 | 1/2012 | Shaw et al. |
| 2012/0029504 A1 | 2/2012 | Afonso et al. |
| 2012/0071870 A1 | 3/2012 | Salahieh et al. |
| 2012/0095347 A1 | 4/2012 | Adam et al. |
| 2012/0101398 A1 | 4/2012 | Ramanathan et al. |
| 2012/0116537 A1 | 5/2012 | Liebetanz |
| 2012/0136346 A1 | 5/2012 | Condie et al. |
| 2012/0136348 A1 | 5/2012 | Condie et al. |
| 2012/0136351 A1 | 5/2012 | Weekamp et al. |
| 2012/0165702 A1 | 6/2012 | Hauck |
| 2012/0172698 A1 | 7/2012 | Teo et al. |
| 2012/0172727 A1 | 7/2012 | Hastings et al. |
| 2012/0172871 A1 | 7/2012 | Hastings et al. |
| 2012/0232460 A1 | 9/2012 | Raven et al. |
| 2012/0238897 A1 | 9/2012 | Wilfley et al. |
| 2012/0310064 A1 | 12/2012 | McGee |
| 2012/0323237 A1 | 12/2012 | Paul et al. |
| 2012/0330304 A1 | 12/2012 | Vegesna et al. |
| 2013/0023784 A1 | 1/2013 | Schneider et al. |
| 2013/0023897 A1 | 1/2013 | Wallace |
| 2013/0060245 A1 | 3/2013 | Grunewald et al. |
| 2013/0066312 A1 | 3/2013 | Subramaniam et al. |
| 2013/0066315 A1 | 3/2013 | Subramaniam et al. |
| 2013/0079763 A1 | 3/2013 | Heckel et al. |
| 2013/0085416 A1 | 4/2013 | Mest |
| 2013/0138099 A1 | 5/2013 | Paul et al. |
| 2013/0165926 A1 | 6/2013 | Mathur et al. |
| 2013/0172715 A1 | 7/2013 | Just et al. |
| 2013/0172742 A1 | 7/2013 | Rankin et al. |
| 2013/0172875 A1 | 7/2013 | Govari et al. |
| 2013/0184706 A1 | 7/2013 | Gelbart et al. |
| 2013/0190747 A1 | 7/2013 | Koblish et al. |
| 2013/0197363 A1 | 8/2013 | Rankin et al. |
| 2013/0197507 A1 | 8/2013 | Kim et al. |
| 2013/0226169 A1 | 8/2013 | Miller et al. |
| 2013/0274582 A1 | 10/2013 | Afonso et al. |
| 2013/0331739 A1 | 12/2013 | Gertner |
| 2013/0345537 A1 | 12/2013 | Thakur et al. |
| 2014/0012251 A1 | 1/2014 | Himmelstein et al. |
| 2014/0051959 A1 | 2/2014 | Gliner et al. |
| 2014/0058375 A1 | 2/2014 | Koblish |
| 2014/0066764 A1 | 3/2014 | Subramaniam et al. |
| 2014/0073893 A1 | 3/2014 | Bencini |
| 2014/0075753 A1 | 3/2014 | Haarer et al. |
| 2014/0081111 A1 | 3/2014 | Tun et al. |
| 2014/0081112 A1 | 3/2014 | Kim et al. |
| 2014/0081113 A1 | 3/2014 | Cohen et al. |
| 2014/0081262 A1 | 3/2014 | Koblish et al. |
| 2014/0100563 A1 | 4/2014 | Govari et al. |
| 2014/0107430 A1 | 4/2014 | Deno et al. |
| 2014/0107453 A1 | 4/2014 | Maskara et al. |
| 2014/0107636 A1 | 4/2014 | Bencini |
| 2014/0121660 A1 | 5/2014 | Hauck |
| 2014/0128757 A1 | 5/2014 | Banet et al. |
| 2014/0142393 A1 | 5/2014 | Piskun et al. |
| 2014/0194867 A1 | 7/2014 | Fish et al. |
| 2014/0200429 A1 | 7/2014 | Spector et al. |
| 2014/0200430 A1 | 7/2014 | Spector |
| 2014/0214028 A1 | 7/2014 | Gelbart et al. |
| 2014/0228713 A1 | 8/2014 | Thao et al. |
| 2014/0243917 A1 | 8/2014 | Morley et al. |
| 2014/0261985 A1 | 9/2014 | Selkee |
| 2014/0275916 A1 | 9/2014 | Nabutovsky et al. |
| 2014/0276052 A1 | 9/2014 | Rankin et al. |
| 2014/0276811 A1 | 9/2014 | Koblish et al. |
| 2014/0288548 A1 | 9/2014 | Kim et al. |
| 2014/0330150 A1 | 11/2014 | Thakur et al. |
| 2014/0336518 A1 | 11/2014 | Shuros et al. |
| 2014/0350694 A1 | 11/2014 | Behan |
| 2014/0358137 A1 | 12/2014 | Hu |
| 2014/0364715 A1 | 12/2014 | Hauck |
| 2014/0364843 A1 | 12/2014 | Paul et al. |
| 2014/0364848 A1 | 12/2014 | Heimbecher et al. |
| 2014/0379093 A1 | 12/2014 | Durgin |
| 2015/0005624 A1 | 1/2015 | Hauck et al. |
| 2015/0011995 A1 | 1/2015 | Avitall et al. |
| 2015/0018813 A1 | 1/2015 | Gliner |
| 2015/0133914 A1 | 5/2015 | Koblish |
| 2015/0133920 A1 | 5/2015 | Rankin et al. |
| 2015/0148796 A1 | 5/2015 | Bencini |
| 2015/0164356 A1 | 6/2015 | Merschon et al. |
| 2015/0224326 A1 | 8/2015 | Toth et al. |
| 2015/0254419 A1 | 9/2015 | Laughner et al. |
| 2015/0265341 A1 | 9/2015 | Koblish |
| 2015/0265348 A1 | 9/2015 | Avitall et al. |
| 2015/0342672 A1 | 12/2015 | Bencini et al. |
| 2015/0374252 A1 | 12/2015 | De et al. |
| 2015/0374436 A1 | 12/2015 | Subramaniam et al. |
| 2016/0008065 A1 | 1/2016 | Gliner et al. |
| 2016/0089256 A1 | 3/2016 | Belhe et al. |
| 2016/0100884 A1 | 4/2016 | Fay et al. |
| 2016/0113582 A1 | 4/2016 | Altmann et al. |
| 2016/0113712 A1 | 4/2016 | Cheung et al. |
| 2016/0174865 A1 | 6/2016 | Stewart et al. |
| 2019/0223951 A1 | 7/2019 | Bencini |
| 2020/0222115 A1 | 7/2020 | Cheung et al. |

FOREIGN PATENT DOCUMENTS

| | | |
|---|---|---|
| CA | 2847846 A1 | 3/2013 |
| CA | 2848053 A1 | 3/2013 |
| CN | 1269708 A | 10/2000 |
| CN | 1455655 A | 11/2003 |
| CN | 1674836 A | 9/2005 |
| CN | 1942145 A | 4/2007 |
| CN | 101045016 A | 10/2007 |
| CN | 101879060 A | 11/2010 |
| CN | 102271607 A | 12/2011 |
| CN | 102573966 A | 7/2012 |
| CN | 102573986 A | 7/2012 |
| CN | 103251451 A | 8/2013 |
| CN | 103917185 A | 7/2014 |
| CN | 103987336 A | 8/2014 |
| CN | 104039257 A | 9/2014 |
| CN | 104244810 A | 12/2014 |
| CN | 104254368 A | 12/2014 |
| CN | 104619259 A | 5/2015 |
| CN | 104640513 A | 5/2015 |
| CN | 104661609 A | 5/2015 |
| EP | 1502542 A1 | 2/2005 |
| EP | 1547537 A1 | 6/2005 |
| EP | 0985423 B1 | 4/2006 |
| EP | 1343427 B1 | 7/2006 |
| EP | 1717601 A2 | 11/2006 |
| EP | 1935332 A2 | 6/2008 |
| EP | 1009303 B1 | 6/2009 |
| EP | 1343426 B1 | 10/2012 |
| EP | 2574278 A2 | 4/2013 |
| EP | 2755587 A2 | 7/2014 |
| EP | 2755588 A1 | 7/2014 |
| EP | 2136702 B1 | 7/2015 |
| EP | 2897545 A1 | 7/2015 |
| JP | 06-507797 A | 9/1994 |
| JP | 07-100214 A | 4/1995 |
| JP | 08-038501 A | 2/1996 |
| JP | 09-140803 A | 6/1997 |
| JP | 2000-000242 A | 1/2000 |
| JP | 2000-083918 A | 3/2000 |
| JP | 2000-504242 A | 4/2000 |
| JP | 2002-528039 A | 8/2002 |
| JP | 2003-504090 A | 2/2003 |

(56) References Cited

FOREIGN PATENT DOCUMENTS

| | | |
|---|---|---|
| JP | 2004-503335 A | 2/2004 |
| JP | 2005-500127 A | 1/2005 |
| JP | 2006-239414 A | 9/2006 |
| JP | 2007-513684 A | 5/2007 |
| JP | 2007-513685 A | 5/2007 |
| JP | 2007-163559 A | 6/2007 |
| JP | 2007-244857 A | 9/2007 |
| JP | 2008-080152 A | 4/2008 |
| JP | 2009-518150 A | 5/2009 |
| JP | 2009-142653 A | 7/2009 |
| JP | 2010-522623 A | 7/2010 |
| JP | 2011-142995 A | 7/2011 |
| JP | 2011-525842 A | 9/2011 |
| JP | 2012-531967 A | 12/2012 |
| JP | 5336465 B2 | 11/2013 |
| JP | 2014-012174 A | 1/2014 |
| JP | 2014-531244 A | 11/2014 |
| JP | 2015-501162 A | 1/2015 |
| JP | 2015-509027 A | 3/2015 |
| KR | 10-2010-0021401 A | 2/2010 |
| KR | 10-1490374 B1 | 2/2015 |
| WO | 92/21278 A1 | 12/1992 |
| WO | 94/13358 A1 | 6/1994 |
| WO | 96/04860 A1 | 2/1996 |
| WO | 97/25916 A1 | 7/1997 |
| WO | 97/25917 A1 | 7/1997 |
| WO | 97/36541 A1 | 10/1997 |
| WO | 97/45156 A2 | 12/1997 |
| WO | 99/02096 A1 | 1/1999 |
| WO | 98/58681 A3 | 3/1999 |
| WO | 99/09879 A1 | 3/1999 |
| WO | 99/27862 A1 | 6/1999 |
| WO | 99/53853 A1 | 10/1999 |
| WO | 00/29062 A2 | 5/2000 |
| WO | 01/41664 A1 | 6/2001 |
| WO | 01/58372 A1 | 8/2001 |
| WO | 01/64145 A1 | 9/2001 |
| WO | 01/68173 A2 | 9/2001 |
| WO | 01/74252 A2 | 10/2001 |
| WO | 01/80755 A2 | 11/2001 |
| WO | 02/02234 A1 | 1/2002 |
| WO | 02/05868 A2 | 1/2002 |
| WO | 02/09599 A2 | 2/2002 |
| WO | 02/19934 A1 | 3/2002 |
| WO | 02/47569 A1 | 6/2002 |
| WO | 2002/102234 A2 | 12/2002 |
| WO | 03/39338 A2 | 5/2003 |
| WO | 2004/093703 A1 | 11/2004 |
| WO | 2007/079278 A1 | 7/2007 |
| WO | 2008/003058 A2 | 1/2008 |
| WO | 2008/046031 A2 | 4/2008 |
| WO | 2008/118992 A1 | 10/2008 |
| WO | 2009/032421 A2 | 3/2009 |
| WO | 2009/048824 A1 | 4/2009 |
| WO | 2009/048943 A1 | 4/2009 |
| WO | 2010/001595 A1 | 1/2010 |
| WO | 2010/054409 A1 | 5/2010 |
| WO | 2010/056771 A1 | 5/2010 |
| WO | 2010/082146 A1 | 7/2010 |
| WO | 2011/008444 A1 | 1/2011 |
| WO | 2011/024133 A1 | 3/2011 |
| WO | 2011/033421 A1 | 3/2011 |
| WO | 2011/089537 A1 | 7/2011 |
| WO | 2011/095937 A1 | 8/2011 |
| WO | 2011/101778 A1 | 8/2011 |
| WO | 2012/001595 A1 | 1/2012 |
| WO | 2012/049621 A1 | 4/2012 |
| WO | 2012/066430 A1 | 5/2012 |
| WO | 2012/135703 A2 | 10/2012 |
| WO | 2012/151301 A1 | 11/2012 |
| WO | 2012/161880 A1 | 11/2012 |
| WO | 2012/166239 A1 | 12/2012 |
| WO | 2013/040201 A2 | 3/2013 |
| WO | 2013/040297 A1 | 3/2013 |
| WO | 2013/101923 A1 | 7/2013 |
| WO | 2014/036439 A2 | 3/2014 |
| WO | 2014/047281 A1 | 3/2014 |
| WO | 2014/058375 A2 | 4/2014 |
| WO | 2014/072879 A2 | 5/2014 |
| WO | 2014/152575 A2 | 9/2014 |
| WO | 2015/138465 A1 | 9/2015 |
| WO | 2015/143061 A1 | 9/2015 |
| WO | 2015/183635 A1 | 12/2015 |

OTHER PUBLICATIONS

Extended European Search Report issued in EP Application No. 15174537.9, dated Mar. 2, 2016, 7 pages.

Extended European Search Report issued in EP18177491.0, dated Oct. 26, 2018, 10 pages.

Goldbert, S. Nahum et al., "Variables Affecting Proper System Grounding for Radiofrequency Ablation in an Animal Model", JVIR, vol. 11, No. 8, Sep. 2000, pp. 1069-1075.

Hayerkamp, W., et. al. Coagulation of Ventricular Myocardium Using Radiofrequency Alternating Current: Bio-Physical Aspects and Experimental Findings. PACE, 12:187-195, Jan. 1989, Part II.

International Search Report and Written Opinion issued in PCT/US2008/058324, dated Aug. 18, 2008, 11 pages.

International Search Report and Written Opinion issued in PCT/US2012/031819, dated Sep. 27, 2012, 16 pages.

International Search Report and Written Opinion issued in PCT/US2012/055155, dated Mar. 11, 2013, 19 pages.

International Search Report and Written Opinion issued in PCT/US2012/055309, dated Nov. 19, 2012, 13 pages.

International Search Report and Written Opinion issued in PCT/US2012/072061, dated Mar. 21, 2013, 9 pages.

International Search Report and Written Opinion issued in PCT/US2013/020503, dated Mar. 20, 2013, 10 pages.

International Search Report and Written Opinion issued in PCT/US2013/021013, dated Apr. 5, 2013, 14 pages.

International Search Report and Written Opinion issued in PCT/US2013/056211, dated Jan. 20, 2014.

International Search Report and Written Opinion issued in PCT/US2013/058105, dated Nov. 22, 2013, 16 pages.

International Search Report and Written Opinion issued in PCT/US2013/060183, dated Jan. 27, 2014, 10 pages.

International Search Report and Written Opinion issued in PCT/US2013/060194, dated Jan. 29, 2014, 10 pages.

International Search Report and Written Opinion issued in PCT/US2013/060612, dated Feb. 28, 2014, 16 pages.

International Search Report and Written Opinion issued in PCT/US2014/027491, dated Sep. 23, 2014, 17 pages.

International Search Report and Written Opinion issued in PCT/US2015/021300, dated Jun. 9, 2015, 11 pages.

International Search Report and Written Opinion issued in PCT/US2015/031591, dated Aug. 17, 2015, 11 pages.

International Search Report and Written Opinion issued in PCT/US2015/055173, dated Jan. 18, 2016, 11 pages.

International Search Report and Written Opinion issued in PCT/US2015/057242, dated Jan. 15, 2016, 11 pages.

International Search Report and Written Opinion issued in PCT/US2015/066874, dated Apr. 1, 2016, 11 pages.

International Search Report and Written Opinion issued in PCT/US2016/028006 dated Jul. 12, 2016, 12 pages.

International Search Report and Written Opinion received for PCT Patent Application No. PCT/US2010/023574, dated Jun. 18, 2010, 11 pages.

Invitation to Pay Additional Fees and Partial International Search Report issued in PCT/US2014/027491, dated Jul. 28, 2014, 5 pages.

IPO First Examination Report issued in Patent Application No. 201717007706, dated Mar. 11, 2020, 7 pages.

Machi MD, Junji, "Prevention of Dispersive Pad Skin Burns During RFA by a Simple Method", Editorial Comment, Surg Laparosc Endosc Percutan Tech , vol. 13, No. 6, Dec. 2003, pp. 372-373.

Neufeid, Gordon R, et al., "Electrical Impedance Properties of the Body and the Problem of Aiternate-site Burns During Electrosurgery", Medical Instrumentation, vol. 19, No. 2, Mar.-Apr. 1985, pp. 83-87.

(56) References Cited

OTHER PUBLICATIONS

Partial European Search Report issued in EP Application 18177491.0, dated Jul. 16, 2018, 11 pages.
Partial International Search Report issued in PCT/US2012/055155, dated Dec. 20, 2012, 7 pages.
Patriciu, A. et al., "Detecting Skin Burns Induced by Surface Electrodes", published in Engineering in Medicine and Biology Society, 2001, Proceedings of the 23rd Annual International Conference of the IEEE, vol. 3, pp. 3129-3131.
Piorkowski, Christopher et al., "First in Human Validation of Impedance-Based Catheter Tip-to-Tissue Contact Assessment in the Left Atrium", Journal of Cardiovascular Electrophysiology, vol. 20, No. 12, Dec. 1, 2009, pp. 1366-1373.
Pires, L. A. et al. Temperature-guided Radiofrequency Catheter Ablation of Closed-Chest Ventricular Myocardium with a Novel Thermistor-Tipped Catheter American Heart Journal, 127(6): 1614-1618, Jun. 1994.
Price, Adam et al., "Novel Abalation Catheter Technology that Improves Mapping Resolution and Monitoring of Lesion Maturation", The Journal of Innovations in Cardiac Rhythm Management, vol. 3, 2002, pp. 599-609.
Price, Adam et al., "PO3-39 Pin Electrodes Improve Resolution: Enhanced Monitoring of Radioirequency Lesions in the Voltage and Frequency Domains", Heart Rhythm 2010, 31st Annual Scientific Sessions, May 12-15 in Denver Colorado.
Ring, E.R., et. Al. Catheter Ablation of the Ventricular Septum with Radiofrequency Energy. American Heart Journal, 117 (6): 1233-1240, Jun. 1989.
Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.
Zachary, J.M. et al., "PO4-86 Pin Electrodes Provide Enhanced Resolution Enabling titration of Radiofrequency Duration to Lesion Maturation", Heart Rhythm 2011, 32 Annual Scientific Sessions, May 4-7, San Francisco, CA.
Woodard et al., Probiotics Improve Outcomes After Roux-en-Y Gastric Bypass Surgery: A Prospective Randomized Trial, J Gastrointest Surg (2009) 13:1198-1204.

\* cited by examiner

TISSUE DIAGNOSIS AND TREATMENT USING MINI-ELECTRODES

CROSS-REFERENCE TO RELATED APPLICATION

This application is a continuation application of U.S. patent application Ser. No. 14/881,112, filed Oct. 12, 2015, which claims priority to Provisional Application No. 62/063,296, filed Oct. 13, 2014, which is herein incorporated by reference in its entirety.

TECHNICAL FIELD

The present disclosure pertains to medical devices, and methods for manufacturing medical devices. More particularly, the present disclosure pertains to tissue diagnosis and/or ablation.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example electrophysiology medical device may include a catheter shaft including a distal end portion and a sensing assembly having three or more terminals. The sensing assembly includes one or more current-carrying electrodes and one or more sensing electrodes. The one or more current-carrying electrodes, the one or more sensing electrodes, or both includes a mini-electrode. The mini-electrode is disposed on one of the other electrodes. The medical device may also include a controller coupled to the sensing assembly.

Additionally or alternatively to any of the examples above, the sensing assembly includes four terminals.

Additionally or alternatively to any of the examples above, one or more of the three or more terminals are disposed along the distal end portion of the catheter shaft.

Additionally or alternatively to any of the examples above, one or more of the three or more terminals are disposed along a device separate from the catheter shaft.

Additionally or alternatively to any of the examples above, one or more current-carrying electrodes includes at least one mini-electrode.

Additionally or alternatively to any of the examples above, one or more current-carrying electrodes includes at least two mini-electrodes.

Additionally or alternatively to any of the examples above, one or more sensing electrodes includes one mini-electrode.

Additionally or alternatively to any of the examples above, one or more sensing electrodes includes two mini-electrodes.

Additionally or alternatively to any of the examples above, one or more current-carrying electrodes includes a mini-electrode and one or more sensing electrodes includes two mini-electrodes.

Additionally or alternatively to any of the examples above, one or more current-carrying electrodes includes two mini-electrodes and one or more sensing electrodes includes a mini-electrode.

Additionally or alternatively to any of the examples above, one or more current-carrying electrodes includes two mini-electrodes and one or more sensing electrodes includes two mini-electrodes.

Additionally or alternatively to any of the examples above, one or more current-carrying electrodes or one or more sensing electrodes includes an ablation electrode.

Additionally or alternatively to any of the examples above, one or more current-carrying electrodes includes an ablation electrode and one or more sensing electrodes includes an electrode disposed on the ablation electrode.

Additionally or alternatively to any of the examples above, one or more sensing electrodes includes an ablation electrode and one or more current-carrying electrodes includes an electrode disposed on the ablation electrode.

Additionally or alternatively to any of the examples above, one or more current-carrying electrodes or one or more sensing electrodes includes a ring electrode.

Additionally or alternatively to any of the examples above, one or more current-carrying electrodes includes an ablation electrode and a ring electrode and the one or more sensing electrodes includes at least one mini-electrode.

Additionally or alternatively to any of the examples above, one or more current-carrying electrodes includes at least one mini-electrode and one or more sensing electrodes includes an ablation electrode and a ring electrode.

Additionally or alternatively to any of the examples above, one or more current-carrying electrodes includes an ablation electrode and a mini-electrode and one or more sensing electrodes includes a ring electrode and a mini-electrode.

Additionally or alternatively to any of the examples above, one or more current-injecting electrodes includes a ring electrode and a mini-electrode and one or more sensing electrodes includes an ablation electrode and a mini-electrode.

Another example electrophysiology medical device may include a catheter shaft including a distal end portion. The distal end portion includes a plurality of electrodes. The plurality of electrodes includes at least one current-carrying electrode, a first sensing electrode and a second sensing electrode. Further, at least one of the electrodes is a mini-electrode disposed on another one of the other electrodes. The first sensing electrode is spaced from the current-carrying electrode a first distance. The second sensing electrode is spaced from the current-carrying electrode a second distance and the first distance is different from the second distance.

Additionally or alternatively to any of the examples above, the medical device may include a controller coupled to the plurality of electrodes. The at least one current-carrying electrode and the first and second sensing electrodes are arranged in a four-terminal sensing configuration and the controller is capable of calculating a parameter capable of indicating the proximity of the medical device to tissue.

An example method for diagnosing and/or treating a condition of the heart may include advancing an electrophysiology catheter through a blood vessel to a position adjacent a target site and utilizing the catheter to determine the proximity of the catheter to the target site. The catheter includes a distal end portion and a four-terminal sensing assembly disposed on the distal end portion. The four-terminal sensing assembly includes one or more current-carrying electrodes and one or more sensing electrodes. One or more current-carrying electrodes and/or the one or more sensing electrodes includes a mini-electrode. The method may also include a controller coupled to the four-terminal sensing assembly.

The above summary of some embodiments is not intended to describe each disclosed embodiment or every implementation of the present disclosure. The Figures, and Detailed Description, which follow, more particularly exemplify these embodiments.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The disclosure may be more completely understood in consideration of the following detailed description in connection with the accompanying drawings, in which.

Figure 1:
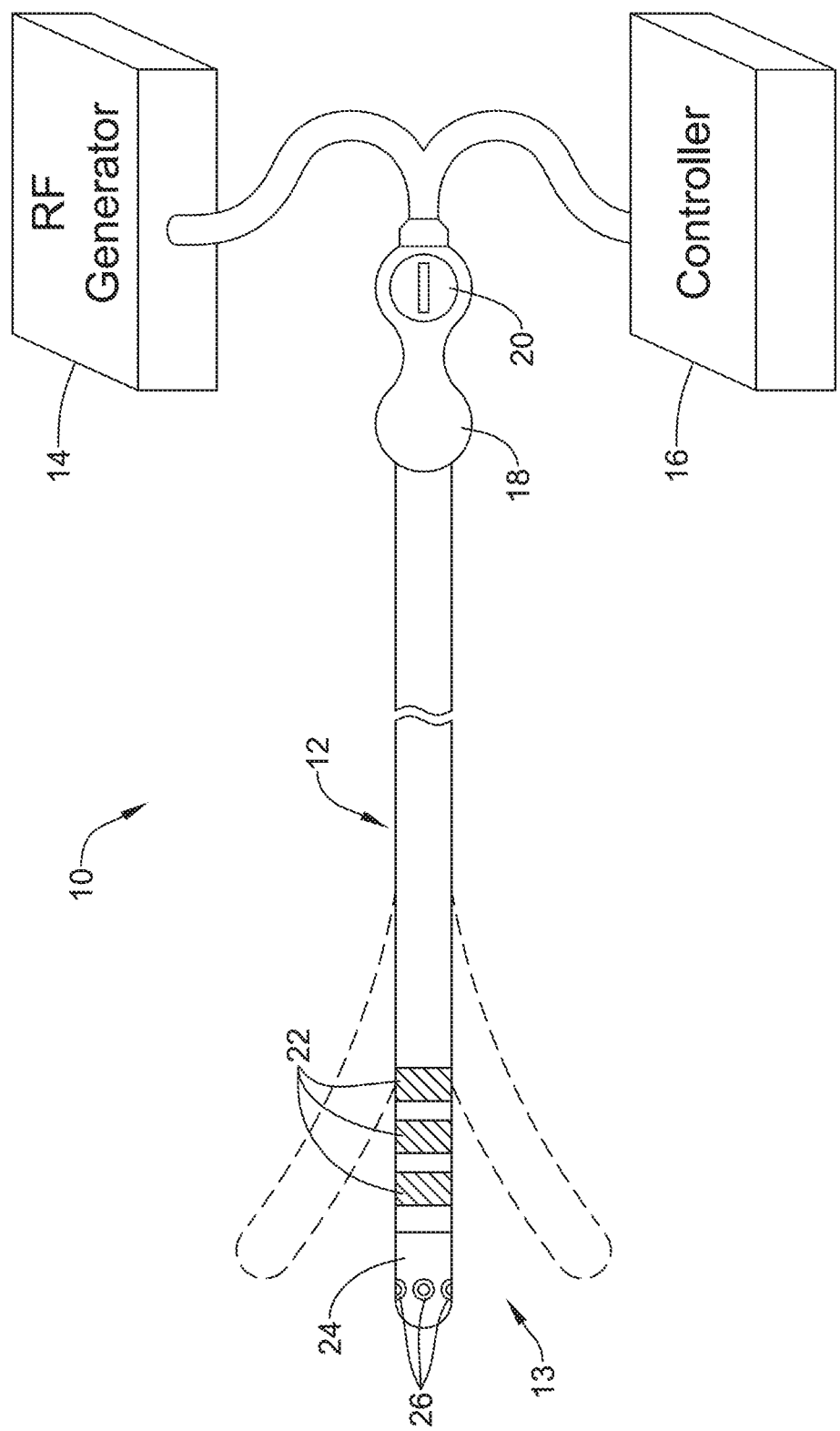
FIG. 1 is a plan view of an example tissue diagnosis and/or ablation system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cardiac arrhythmia and/or other cardiac pathology contributing to abnormal heart function may originate in cardiac cellular tissue. One technique that may be utilized to treat the arrhythmia and/or cardiac pathology may include ablation of tissue substrates contributing to the arrhythmia and/or cardiac pathology. The tissue in the substrate may be electrically disrupted, or ablated, by heat, chemicals or other means of creating a lesion in the tissue, or otherwise can be electrically isolated from the normal heart circuit. Electrophysiology therapy involves locating the tissue contributing to the arrhythmia and/or cardiac pathology using an ablation, mapping and/or diagnosing catheter and then using the ablation catheter (or another device) to destroy and/or isolate the tissue.

Prior to performing an ablation procedure, a physician and/or clinician may utilize specialized mapping and/or diagnostic catheters to precisely locate tissue contributing and/or causing an arrhythmia or other cardiac pathology. It may, therefore, be desirable to be able to precisely locate the targeted tissue prior to performing the ablation procedure in order to effectively alleviate and/or eliminate the arrhythmia and/or cardiac pathology. Further, precise targeting of the tissue may prevent or reduce the likelihood that healthy tissue (located proximate the targeted tissue) is damaged.

Several methods and/or techniques may be employed to precisely locate targeted tissue where an ablation or other therapeutic procedure may be performed. An example method may include utilizing an ablation, mapping and/or diagnostic catheter to determine how close the catheter is to targeted tissue. Further, the ablation, mapping and/or diagnostic catheter may include one or more sensing electrodes located on a distal portion of the catheter. The electrodes may sense, measure and/or provide a controller with information relating to electrical activity within the cardiac tissue. Using the sensed and/or measured electrical information from cardiac tissue, the controller may be able to correlate the spatial location of the distal portion of the catheter in relation to the cardiac tissue. For example, the electrodes may measure the impedance, resistance, voltage potential, etc. and determine how far a distal portion of a diagnostic and/or ablation catheter is to cardiac tissue.

Electrodes utilized in conjunction with an ablation, mapping and/or diagnostic catheter are often located on the distal portion and/or distal end of the catheter. For example, an ablation catheter may include a distal tip electrode and one or more ring electrodes located proximal the distal tip electrode. The distal tip electrode may be able to sense and/or measure electrical activity in addition to being able to provide ablative therapy as an ablation electrode. The ring electrodes may be used as sensing and/or measuring electrodes in conjunction with one another and/or the ablation electrode.

In general, the size and/or spacing of electrodes may contribute to the accuracy of the electrical information sensed and/or measured by the mapping and/or diagnostic catheter. For example, some methods and/or techniques may emit a current from a first electrode and measure the impedance (or other electrical characteristic) of local tissue using a different pair of electrodes. However, a current emitted from an electrode having a large surface area may not be as concentrated as compared to a current emitted from an electrode having a (proportionally) smaller surface area. A smaller electrode surface area may have a tendency to focus and/or direct current to tissue immediately adjacent the emitting and/or measuring electrodes.

Further, in some circumstances it may be challenging to position an ablation tip and/or ring electrodes precisely adjacent targeted tissue due to the relatively large size of the tip and/or a ring electrode. In particular, it may be challenging to arrange larger electrodes in an optimally-spaced configuration because the size and shape of larger electrodes may limit how close the electrodes can be placed to one another.

In addition, larger electrodes may be more susceptible (as compared to smaller electrodes) to detecting far field electrical activity. Detection of far field electrical activity may negatively affect the detection of local (e.g. targeted) electrical activity.

Therefore, it may be desirable in some instances to utilize, dispose, incorporate and/or couple smaller electrodes (e.g. mini-electrodes) into the distal portion of mapping and/or diagnostic catheters. For example, some of the medical devices and methods disclosed herein may include sensing and measuring electrical activity using mini-electrodes alone or in conjunction with ablation electrodes, ring electrodes, catheters and/or other medical devices. Further, some of the medical devices and methods disclosed herein may utilize electrical information collected from mini-electrodes to assess tissue proximity and/or contact. Other methods and medical devices are also disclosed.

FIG. 1 illustrates an example cardiac mapping and/or ablation system 10. As shown in FIG. 1, system 10 may include an elongated member or catheter shaft 12, an RF generator 14, and a controller 16 (e.g., a mapping processor, ablation processor, and/or other processor). Illustratively, shaft 12 may be operatively coupled to at least one or more (e.g., one or both) of RF generator 14 and controller 16. Alternatively, or in addition, a device (other than shaft 12), may be utilized to apply ablation energy and/or diagnose a target area and may be operatively coupled to at least one or more of RF generator 14 and controller 16. RF generator 14 may be capable of delivering and/or may be configured to deliver ablation energy to shaft 12 in a controlled manner in order to ablate target area sites identified by controller 16. Although the controller 16 and RF generator 14 may be shown as discrete components, these components or features of components may be incorporated into a single device. System 10 may include any of one or more other features, as desired.

In at least some embodiments, shaft 12 may include a handle 18, which may have an actuator 20 (e.g., a control knob or other actuator). The handle 18 (e.g., a proximal handle) may be positioned at a proximal end of shaft 12, for example. Illustratively, shaft 12 may include a flexible body having a having a distal portion which may include one or more electrodes. For example, the distal portion of shaft 12 may include one or more of a plurality of ring electrodes 22, a distal ablation tip electrode 24, and a plurality of mini-electrodes 26 disposed or otherwise positioned along and/or electrically isolated from distal ablation tip electrode 24.

Shaft 12 may be steerable to facilitate navigating the vasculature of a patient or navigating other lumens. Illustratively, a distal portion 13 of shaft 12 may be deflected by manipulation of actuator 20 to effect steering shaft 12. In some instances, distal portion 13 of shaft 12 may be deflected to position distal ablation tip electrode 24 and/or mini-electrodes 26 adjacent target tissue or to position the distal portion 13 of shaft 12 for another suitable purpose. Additionally, or alternatively, distal portion 13 of shaft 12 may have a pre-formed shape adapted to facilitate positioning distal ablation tip electrode 24 and/or micro-electrode assemblies 26 adjacent a target tissue. Illustratively, the preformed shape of distal portion 13 of shaft 12 may be a radiused shape (e.g., a generally circular shape or a generally semi-circular shape) and/or may be oriented in a plane transverse to a general longitudinal direction of shaft 12. These are just examples.

In some instances, system 10 may be utilized in ablation procedures on a patient. Illustratively, shaft 12 may be configured to be introduced into or through vasculature of a patient and/or into or through any other lumen or cavity. In one example, shaft 12 may be inserted through the vasculature of the patient and into one or more chambers of the patient's heart (e.g., a target area). When in the patient's vasculature or heart, shaft 12 may be used to map and/or ablate myocardial tissue using the ring electrodes 22, mini-electrodes 26, and/or distal ablation tip electrode 24. In some instances, distal ablation tip electrode 24 may be configured to apply ablation energy to myocardial tissue of the heart of a patient.

Distal ablation tip electrode 24 may be a suitable length and include a suitable surface area. In some instances, distal ablation tip electrode 24 may have a length of between one (1) mm and twenty (20) mm, three (3) mm and seventeen (17) mm, or six (6) mm and fourteen (14) mm. In one illustrative example, distal ablation tip electrode 24 may have an axial length of about eight (8) mm. Further, distal ablation tip electrode may have a suitable surface area of between five (5) $mm^2$ and one hundred (100) $mm^2$, ten (10) $mm^2$ and eighty (80) $mm^2$, or twenty (20) $mm^2$ and seventy (70) $mm^2$. In one illustrative example, distal ablation tip electrode 24 may have a surface area of about twenty-nine (29) $mm^2$. Distal ablation tip electrode 24 may be formed from or otherwise include platinum and/or other suitable materials. These are just examples.

As stated, mini-electrodes 26 may be circumferentially distributed about a distal ablation tip electrode 24. Mini-electrodes 26 may be capable of operating, or configured to operate, in unipolar or bipolar sensing modes. Mini-electrodes 26 may be capable of sensing, or may be configured to sense, electrical characteristics (e.g. impedance) corresponding to myocardial tissue proximate thereto.

For example, in some instances system 10 may be capable of utilizing impedance measurements to sense contact between the catheter tip (e.g. distal ablation tip electrode 24) and tissue. In general, the impedance of a given medium may be measured by applying a known voltage or current to a given medium and measuring the resulting voltage or current. In other words, impedance measurements of a given medium can be obtained by injecting current between two electrodes and measuring the resulting voltage between the same electrodes through which the current was injected. The ratio of the voltage potential to the applied current provides an indication of the impedance of the medium through which the current traveled.

For example, FIG. 1 illustrates that current may be injected between distal ablation tip electrode 24 and a ring electrode 22. Impedance of the medium (e.g. tissue) adjacent to distal ablation tip electrode 24 and ring electrode 22 may be measured according to the methodology disclosed above. For example, if the distal ablation tip electrode 24 and ring electrode are embedded in cardiac tissue, the impedance of the cardiac tissue may be determined.

In some instances, contact system 10 may utilize different impedance measurements of a local medium to determine whether the distal ablation tip electrode 24 is contacting tissue. For example, the impedance of cardiac tissue is different than that of blood. Therefore, by knowing the relative difference in the impedance of tissue versus blood, system 10 may be able to determine whether the medium through which a current is being applied is either blood or cardiac tissue, for example.

In some examples, mini-electrodes 26 may be operatively coupled to controller 16. Further, generated output from mini-electrodes 26 may be sent to controller 16 of system 10 for processing in one or more manners discussed herein and/or for processing in other manners. As stated, an electrical characteristic (e.g. impedance) and/or an output signal from a mini-electrode pair may at least partially form the basis of a contact assessment, ablation area assessment (e.g., tissue viability assessment), and/or an ablation progress assessment (e.g., a lesion formation/maturation analysis), as discussed below.

Further, system 10 may be capable of processing or may be configured to process the electrical signals from mini-electrodes 26, ring electrodes 22, and/or distal ablation tip electrode 24. Based, at least in part, on the processed output from mini-electrodes 26, ring electrodes 22, and/or distal ablation tip electrode 24, controller 16 may generate an output to a display (not shown) for use by a physician or other user. In instances where an output is generated to a display and/or other instances, controller 16 may be operatively coupled to or otherwise in communication with the display. Illustratively, the display may include various static and/or dynamic information related to the use of system 10. In one example, the display may include one or more of an image of the target area, an image of shaft 12, and/or indicators conveying information corresponding to tissue proximity, which may be analyzed by the user and/or by a processor of system 10 to determine the existence and/or location of arrhythmia substrates within the heart, to determine the location of shaft 12 within the heart, and/or to make other determinations relating to use of shaft 12 and/or other elongated members.

System 10 may include an indicator in communication with controller 16. The indicator may be capable of providing an indication related to a feature of the output signals received from one or more of the electrodes of shaft 12. In one example, an indication to the clinician about a characteristic of shaft 12 and/or the myocardial tissue interacted with and/or being mapped may be provided on the display. In some cases, the indicator may provide a visual and/or audible indication to provide information concerning the characteristic of shaft 12 and/or the myocardial tissue interacted with and/or being mapped. For example, system 10 may determine that a measured impedance corresponds to an impedance value of cardiac tissue and therefore may output a color indicator (e.g. green) to a display. The color indicator may allow a physician to more easily determine whether to apply ablative therapy to a given cardiac location. This is just an example. It is contemplated that a variety of indicators may be utilized by system 10.

In the above disclosure, the ability for system 10 to accurately measure impedance values may depend on the relative distribution of current density being applied to a given medium. For example, the size of the electrode from which current is emitted may lead to current diffusion through non-targeted, surrounding tissue. When comparing the current density of two electrodes, one of which is proportionally larger than the other, the electrode with less surface area may concentrate an electrical current to localized tissue to a greater extent than the larger electrode. Therefore, it may be challenging to get accurate current delivery at discrete spatial points in cardiac tissue when utilizing proportionally larger electrodes.

Figure 2:
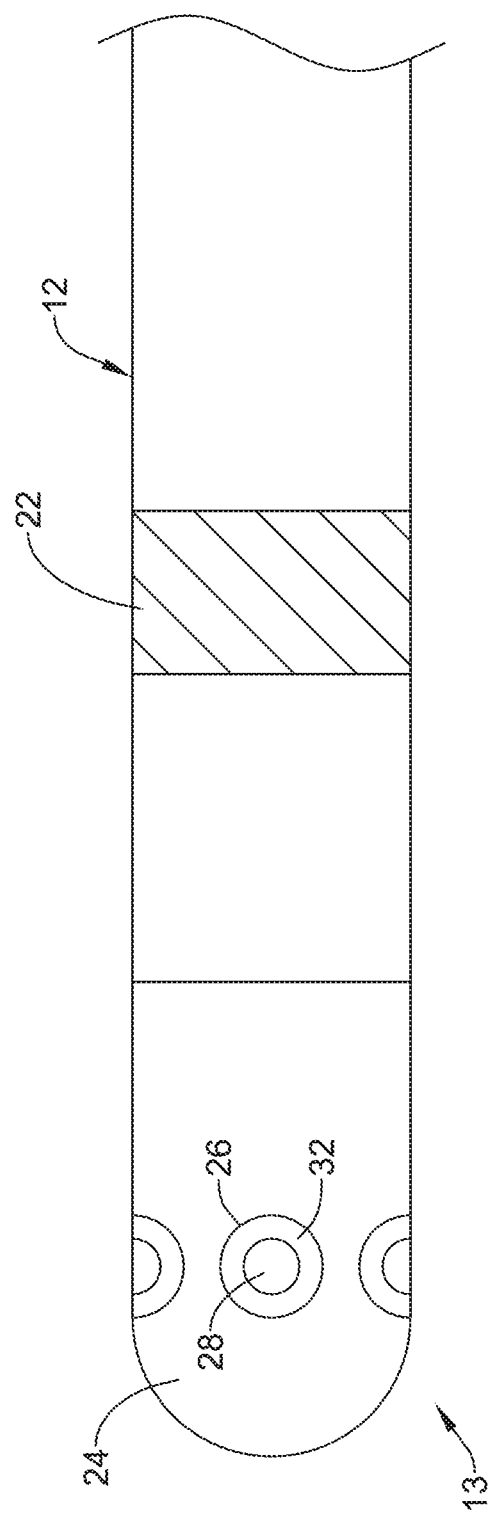
FIG. 2 illustrates an example medical device including a distal tip electrode, a ring electrode and mini-electrodes.

Additional details regarding mini-electrodes 26, distal ablation tip electrode 24 and ring electrode 22 are shown in FIG. 2. FIG. 2 illustrates that mini-electrodes 26 may include "inner" electrode 28. Further, a layer of insulation 32 may be disposed around inner electrode 28. In embodiments where mini-electrodes 26 are disposed along distal ablation tip electrode 24, insulation 32 may insulate inner electrode 28 from distal ablation tip electrode 24, ring electrode 22 and/or other inner electrodes 28. In some embodiments, insulation 32 may surround and isolate inner electrode 28 from ablation tip electrode 24.

As shown in FIG. 2, mini-electrodes 26 may be positioned such that there is minimal space between adjacent mini-electrodes 26. Further, the smaller size of mini-electrodes 26 (relative to distal ablation tip electrode 24, for example) may allow mini-electrodes to be positioned in multiple configurations. For example, mini-electrodes 26 may circumferentially aligned as shown in FIG. 2. Additionally, mini-electrodes 26 may be offset in a variety of different configurations. For example, mini-electrodes 26 may be positioned longitudinally along the longitudinal axis of shaft 12 or may be positioned on the apex of distal ablation tip electrode 24.

It is contemplated that mini-electrodes 26 may have a suitable exposed surface area of between 0.20 mm$^2$ and 1 mm$^2$, 0.30 mm$^2$ and 0.80 mm$^2$, or 0.40 mm$^2$ and 0.70 mm$^2$. In one embodiment, mini-electrodes 26 may have a suitable exposed surface area of 0.50 mm$^2$. Comparison of the ratio of the suitable exposed surface are of mini-electrodes 26 to that of distal ablation tip electrode 24 shows that the suitable exposed surface area of distal ablation tip electrode 24 may be at least ten (10) times larger, fifteen (15) times, or twenty (20) times larger than the suitable surface are of mini-electrodes 26. These are just examples. The ratio of the suitable exposed surface area of distal tip electrode 24 to the suitable exposed surface area of mini-electrode 26 may be less than or greater than twenty (20). For example, the ratio of the suitable exposed surface area of distal tip electrode 24 to the suitable exposed surface area of mini-electrode 26 may be 30, 50, or 100. Further, the ratio of the suitable exposed surface area of distal tip electrode 24 to the suitable exposed surface area of mini-electrode 26 may be less than one hundred seventy five (175).

Alternatively, mini-electrodes 26 may be used in conjunction with distal ablation tip electrode 24, with ring electrode 22, or alone. Additionally, because mini-electrodes 26 may be proportionally smaller than either distal ablation tip electrode 24 and/or ring electrode 22, mini-electrodes 26 may be positioned in many different spatial configurations with respect to distal ablation tip electrode 24 and/or ring electrode 22. For example, as shown in FIG. 2, mini-electrodes 26 may be disposed "on" distal ablation tip electrode 24. As discussed herein, mini-electrodes 26 may be described as being "on," "along," and/or otherwise embedded and/or encased on a given structure. This is not intended to be limiting. Rather, mini-electrodes 26 can be positioned and/or otherwise located at any suitable position/location along the distal tip and/or at other locations along the catheter and/or other remote structure. Positioning/locating the electrodes may include embedding, partially embedding, encasing, partially encasing, isolating, attaching, affixing, fastening, bonding to the outer surface, embedding within the wall, or the like.

Even though much of the discussion herein has been directed to embodiments in which mini-electrodes 26 have been positioned "on" distal ablation tip electrode 24, it is further contemplated that one or more mini-electrodes may be positioned along the catheter shaft at a position that is away from distal ablation tip electrode 24 and continue to function substantially equivalent to those embodiments in which mini-electrodes are positioned "on" distal tip ablation electrode 24.

Figure 3:
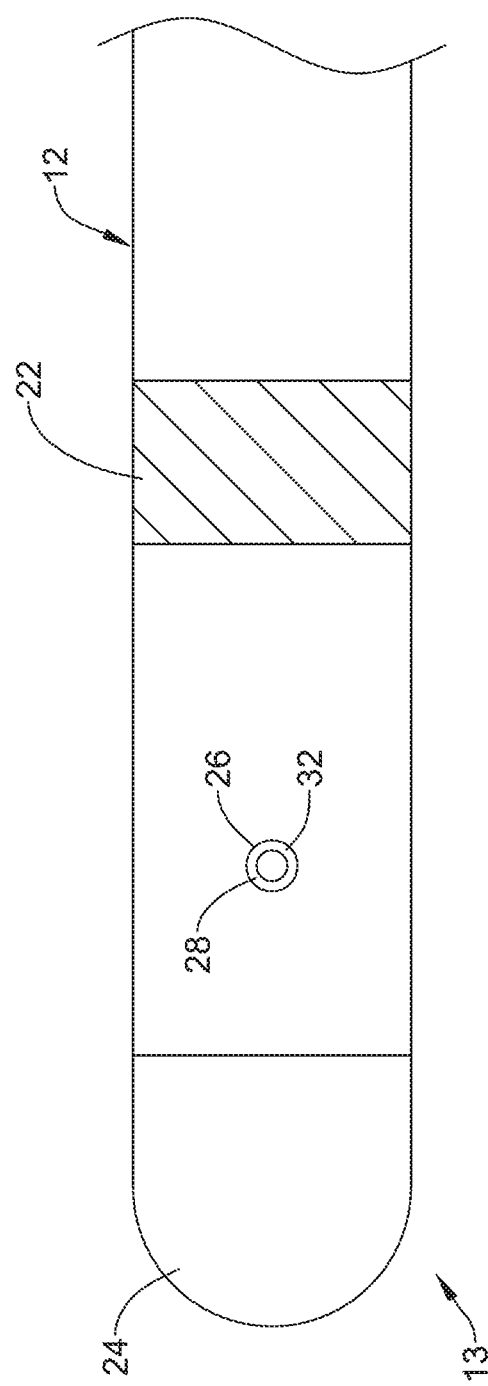
FIG. 3 illustrates an example medical device including a distal tip electrode, a ring electrode and a mini-electrode positioned away from the distal tip electrode and/or ring electrode.

For example, FIG. 3 shows mini-electrode 26 disposed on shaft 12 away from distal ablation tip electrode 24. Further, as discussed above, mini-electrode 26 disposed away from distal ablation tip electrode 24 may be positioned "on" catheter shaft 12 or any other portion of ablation system 10. Additionally, mini-electrodes 26 may be "on" other electrodes (e.g. ring electrode, etc.). As stated above, mini-electrode 26 may be substantially smaller than distal ablation tip electrode 24. As illustrated in FIG. 3, mini-electrode 26 is substantially smaller than distal ablation tip electrode 24.

Further, the size of mini-electrodes 26 may allow mini-electrodes 26 to be placed directly adjacent to tissue for which an ablation, diagnostic and/or therapeutic procedure may be performed. For example, as discussed above, in order to determine tissue contact through impedance measurements, the current for which a voltage ratio (and hence, impedance) is measured must pass through the medium (e.g. tissue) for which the targeted impedance value is sought. If the current is diffused and/or passes primarily through a non-targeted medium (e.g. blood), the observed impedance value may not accurately represent whether the catheter is in contact with the desired medium (e.g. tissue).

Due to their relatively small size, mini-electrodes 26 may be placed precisely at a discrete point in space. Further, it may be desirable to inject current between mini-electrodes 26 positioned at a discrete point in space. It can be appreciated that measurements (e.g. impedance) derived from mini-electrodes 26 may reflect the medium adjacent to a discrete point in space. For example, positioning and driving current through closely positioned mini-electrodes 26 may provide greater confidence that impedance measurements derived therefrom are accurate.

Further, it may be desirable to position mini-electrodes 26 close to distal ablation tip electrode 24 and/or ring electrode 22. For example, disposing closely-positioned mini-electrodes 26 directly on distal ablation tip 24 may provide confidence that distal ablation tip 24 is, in fact, in contact with a given medium reflected by a particular impedance measurement.

As stated above, injecting current through mini-electrodes 26 (versus a larger distal ablation tip electrode 24 and/or ring electrode 22) may improve measurements by concentrating the current path precisely through a localized medium. Diffusion of current through surrounding tissue may be reduced by injecting current through the smaller surface area of mini-electrode 26 verses a larger surface area electrode.

Additionally or alternatively, improvement in the measurement of impedance may be accomplished by using a four-terminal sensing configuration. In general, a four-terminal sensing configuration drives current through a pair of electrodes (similar to that discussed above) and measures the voltage across a different pair of electrodes. For ease of understanding the foregoing discussion, the electrode pair between which current is injected in a four-terminal sensing configuration will be hereafter referred to as the "current-carrying" electrode pair. The electrode pair across which voltage is measured will be referred to as the "sensing" electrode pair.

One advantage of a four-terminal sensing configuration is that the measured impedance may not be sensitive to the impedance of the electrodes. In a two-terminal sensing configuration, the measured impedance includes the surrounding medium and both electrodes. In contrast, a four-terminal sensing configuration measures voltage across electrodes through which the current is negligible. As a result, the measured impedance is that of the surrounding medium and is largely independent of the impedance of the electrode and its interface with the surrounding medium.

Figure 4:
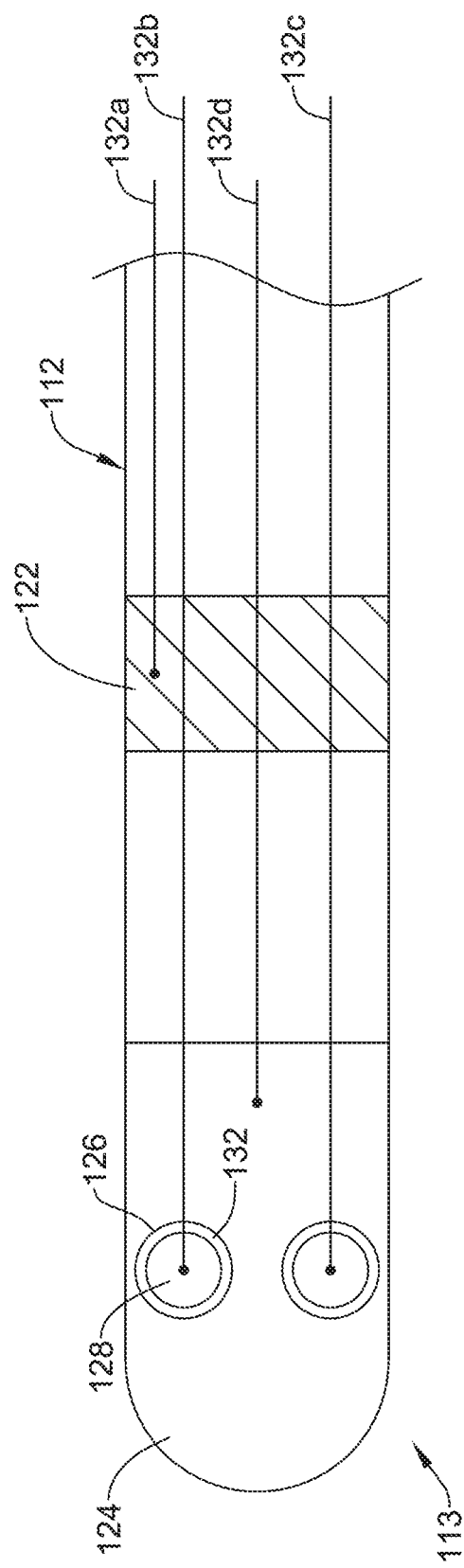
FIG. 4 illustrates an example medical device including a distal tip electrode, a ring electrode and mini-electrodes arranged in a four-terminal sensing configuration.

For example, FIG. 4 illustrates a four-terminal sensing configuration using distal ablation tip electrode 124, ring electrode 122 and two mini-electrodes 126. Additionally, FIG. 4 shows lead wires 132a-132d. Lead wires 132a-132d may connect any given electrode to controller 16, RF generator 14 or both. Lead wires 132a-132d may also connect individual electrodes to one another in a variety of configurations.

Referring to FIG. 4, the distal ablation tip electrode 124 and ring electrode 122 may define the current-carrying electrode pair. Further, the pair of mini-electrodes 126 may define the sensing electrode pair. Therefore, current may be injected between the distal ablation tip electrode 126 and the ring electrode 122, and voltage may be measured across mini-electrodes 126. It can be appreciated that in this example, impedance measurements may be the impedance of the medium adjacent the sensing electrode pair. For example, if the distal portion 13 of system 10 is embedded in tissue, mini-electrodes 126 may measure the impedance of tissue adjacent mini-electrodes 126. It should be understood that one advantage of using a four-terminal system with mini-electrodes 126 is that precise measurements of impedance (or other electrical characteristics) may be obtained at a discrete point.

Additionally or alternatively, a variety of combinations, arrangements and/or configurations may incorporate a variety of electrodes (e.g. distal ablation tip electrode, ring electrode, mini-electrode, remote reference electrode, etc.) in a four-terminal sensing configuration. In some combinations (e.g. the combinations illustrated in FIG. 3 or FIG. 4), the electrodes may be disposed on distal portion 13/113 of catheter shaft 12/112. In other combinations, one or more of the electrodes in a four-terminal sensing configuration may not be disposed on catheter shaft 12/112 and/or distal portion 13/113. Rather, some electrodes may be located off of and away from catheter shaft 12/112 and/or distal portion 13/113.

Figure 5:
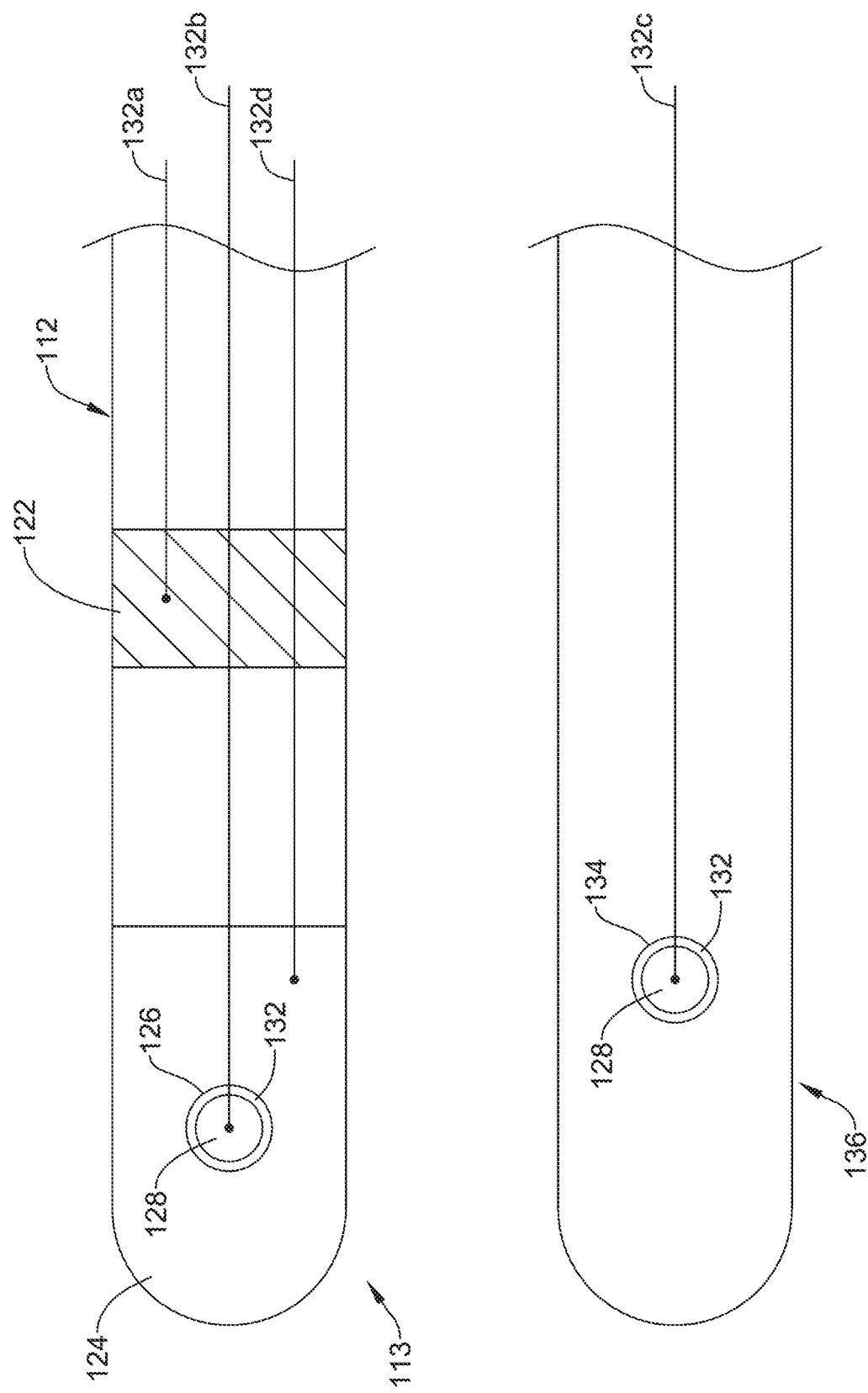
FIG. 5 illustrates two example medical devices arranged in a four-terminal sensing configuration having one mini-electrode positioned separate from an ablation electrode and/or ring electrode.

For example, FIG. 5 shows electrode 134 located away from catheter shaft 112 and distal portion 113. In this example, electrode 134 is located on catheter shaft 136, which is different from or otherwise separate from catheter shaft 112. Even though FIG. 5 shows electrode 134 disposed on catheter shaft 136, it is contemplated that electrode 134 may be located or disposed on any structure away from catheter shaft 112. For example, electrode 134 may be disposed on the surface of a patient's body or disposed on another portion of ablation system 10. These are just examples, other combinations and/or remote structures are contemplated.

Similar to that discussed above with respect to FIGS. 2-4, one or more of the electrodes in a four-terminal sensing configuration that are remote and/or disposed away from catheter shaft 112 may be positioned "on" the structure in which they are disposed. Further, as stated above, any given electrode may be disposed on another electrode yet operate independently of the electrode on which it is disposed (e.g. mini-electrodes 126 disposed on and insulated from distal ablation tip electrode 124).

Additionally or alternatively, a four-terminal sensing configuration may be implemented and/or configured using only three electrodes. In some instances, a single electrode (e.g. distal ablation tip electrode, ring electrode, mini-electrode, remote electrode, etc.) may operate as both a current-carrying and sensing electrode. In this case, the measured impedance may include the impedance of the electrode used for both purposes (e.g., current-carrying and sensing) as well as the impedance of the electrode's interface with the surrounding medium. This configuration may approximate the four-terminal configuration if the impedance of the electrode is low or is not expected to vary significantly. Including the impedance of one of the electrodes (and its interface) may be desirable in some cases, particularly if that impedance varies significantly with tissue contact.

Figure 6:
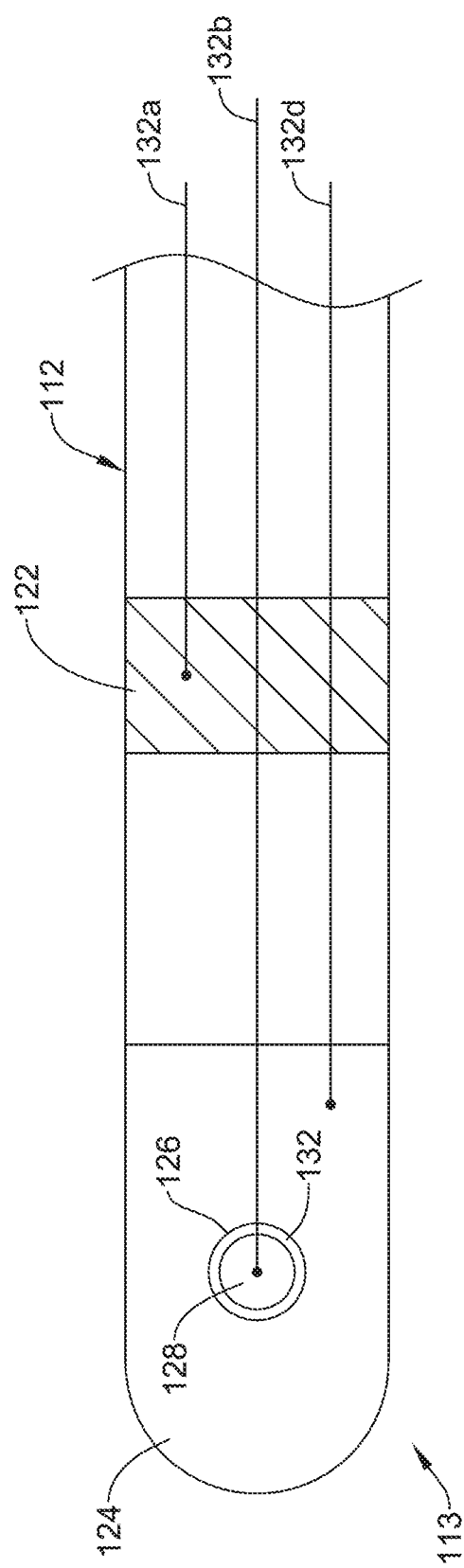
FIG. 6 illustrates an example medical device including a distal tip electrode, a ring electrode and mini-electrodes arranged in a three-terminal sensing configuration.
Figure 7:
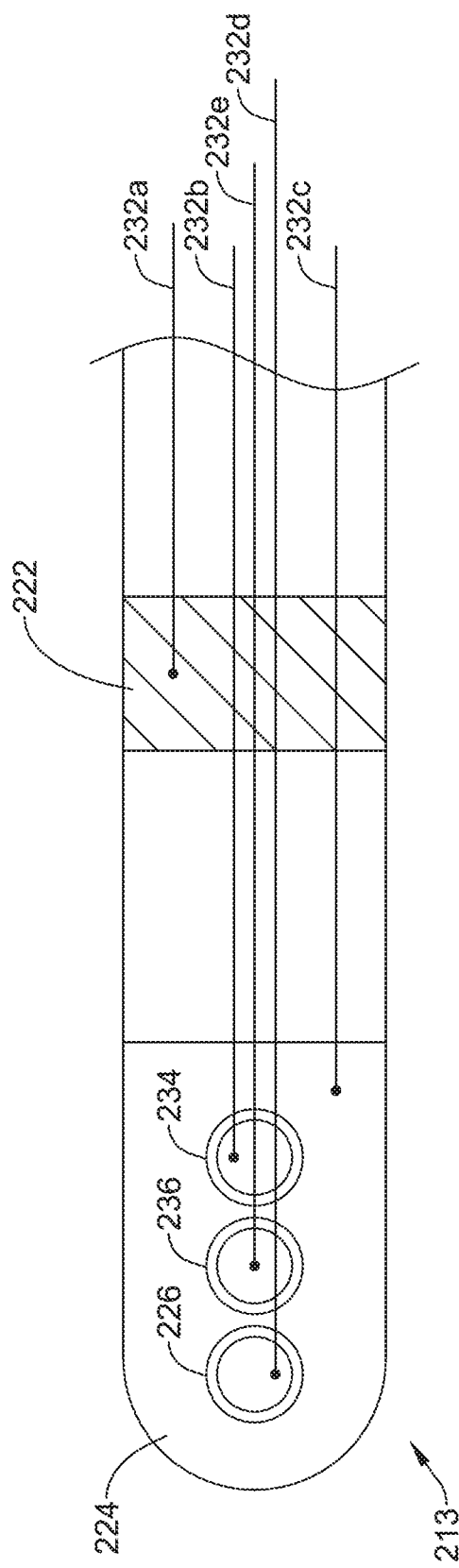
FIG. 7 illustrates an example medical device including a current injecting electrode and four potential measuring electrodes.
Figure 8A:
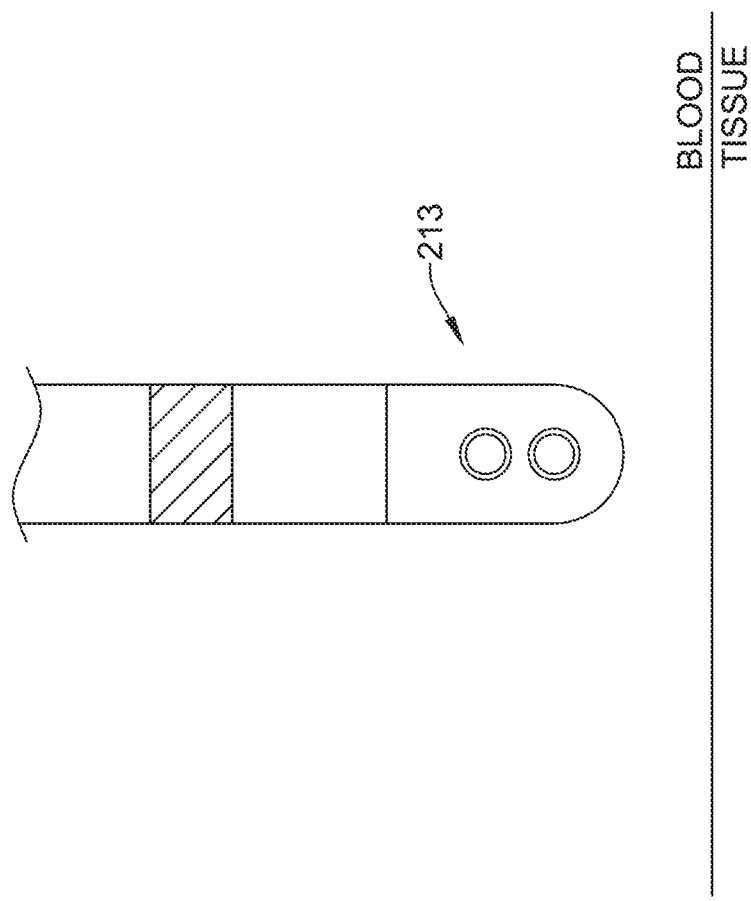
FIGS. 8*a*-8*c* illustrates an example medical device positioned relative to two different mediums.
Figure 8B:
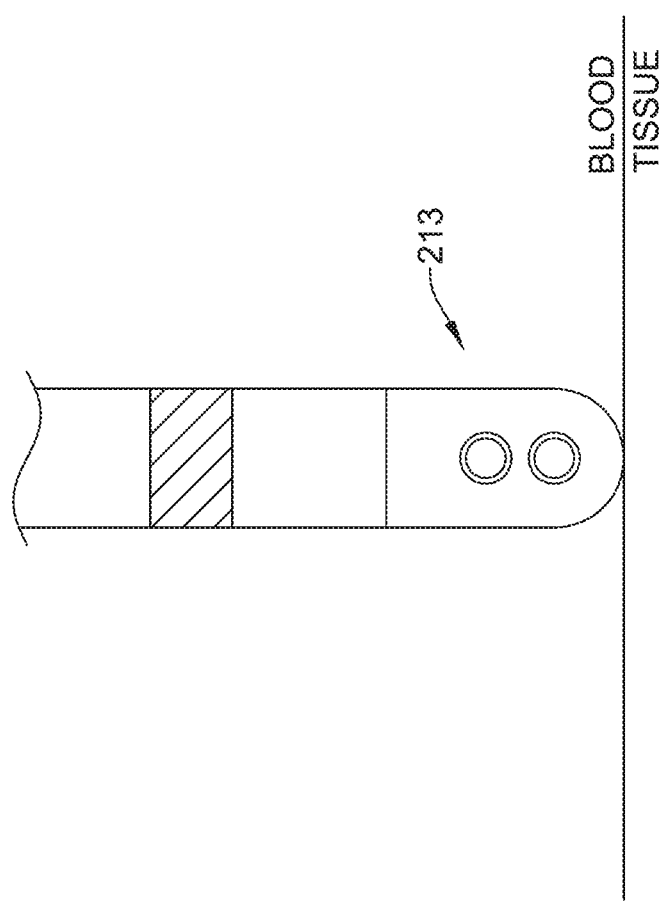
Figure 8C:
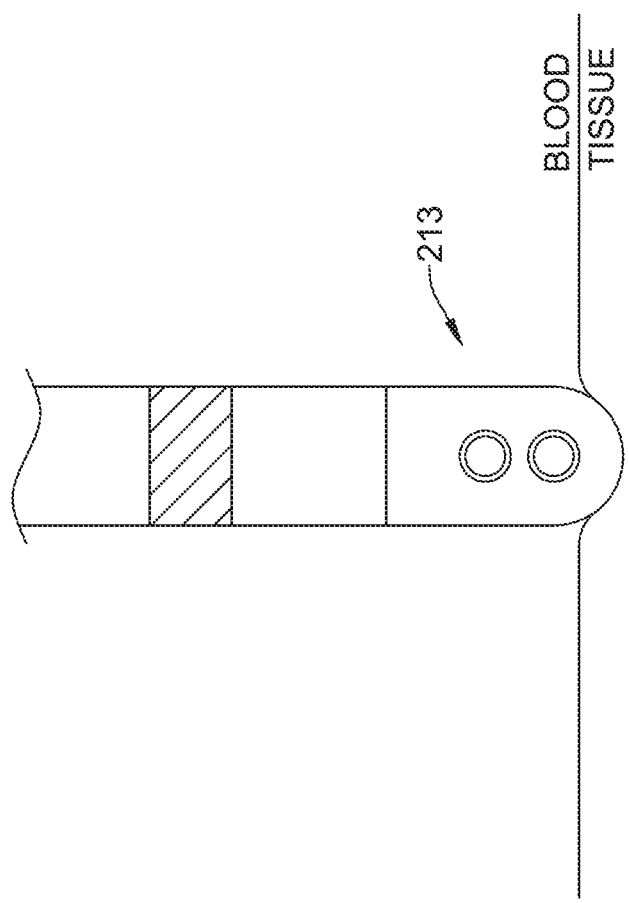

FIG. 6 illustrates a three-terminal sensing configuration. In FIG. 6, any one of distal ablation tip electrode 124, mini-electrode 126 or ring electrode 122 may operate as both a current-carrying and sensing electrode. Further, any of the embodiments and/or configurations discussed with respect to FIGS. 2-5 (e.g. the four-terminal sensing configuration) may be implemented in the three-terminal configuration.

In another example of a four-terminal sensing configuration, the current-carrying electrode pair may include one or more mini-electrodes 126, while the sensing electrode pair may include the distal tip ablation electrode 124 and/or ring electrode 122.

In another example of a four-terminal sensing configuration, the current-carrying electrode pair may include a distal tip ablation electrode 124 and a mini-electrode 126, while the sensing electrode pair may include one or more mini-electrodes 126.

In another example of a four-terminal sensing configuration, the current-carrying electrode pair may include one or more mini-electrodes 126, while the sensing electrode pair may include a distal tip ablation electrode 124 and one or more mini-electrodes 126.

In another example of a four-terminal sensing configuration, the current-carrying electrode pair may include one or more mini-electrodes 126, while the sensing electrode pair may include a ring electrode 122 and one or more mini-electrodes 126.

In another example of a four-terminal sensing configuration, the current-carrying electrode pair may include a ring electrode 122 and one or more mini-electrodes 126, while the sensing electrode pair may include one or more mini-electrodes 126.

In another example of a four-terminal sensing configuration, all the electrodes in the four-terminal sensing configuration may be mini-electrodes 126.

In another example of a four-terminal sensing configuration, the current-carrying electrode pair may include one mini-electrode 126 and distal tip ablation electrode 124, while the sensing electrode pair may include one or more mini-electrode 126 and ring electrode 122.

In another example of a four-terminal sensing configuration, the sensing electrode pair may include one mini-electrode 126 and distal tip ablation electrode 124, while the current-carrying electrode pair may include one or more mini-electrode 126 and ring electrode 122.

In another example of a four-terminal sensing configuration, the current-carrying electrode pair may include one mini-electrode 126, while the sensing electrode pair may include the distal tip ablation electrode 124.

In another example of a four-terminal sensing configuration, the sensing electrode pair may include one mini-electrode 126, while the current-carrying electrode pair may include the distal tip ablation electrode 124.

It is contemplated that the controller 16 may incorporate an algorithm that controls the various electrodes in the desired manner in order to assess contact. This might include powering the electrodes in the manner disclosed herein. This may also include more than one sensing configuration, with the sensing configurations multiplexed in time, frequency, or both.

While the above discussion indicates that mini-electrodes may be used for tissue contact sensing, this is not intended to be limiting. Rather, the mini-electrodes may be used for a variety of functions including ablation, mapping, sensing, or the like.

As stated, the impedance, resistance, voltage and/or other output obtained from any of the above described four-terminal sensing configurations may be displayed for diagnostic use by a physician or clinician. For example, a four-terminal sensing configuration may measure and/or sense the impedance of tissue, and output a corresponding indicator (as described above) to a display. The display may be connected to controller 16, RF generator 14 and/or to any other component of system 10.

In addition or alternatively to that disclosed above, another method for assessing tissue contact may include determining a parameter of a model and observing changes in the parameter as the distal end portion 13 of catheter 12 moves between different mediums (e.g. as between blood and tissue).

For example, a scaling factor may be a parameter in a model used for this purpose. The model may relate to one or more potential differences between one or more sensing electrodes and a reference electrode. A reference electrode may be an electrode placed a distance away from the potential measuring electrodes. For example, a reference electrode may be placed on the back of a patient.

Sensing electrodes may be disposed on the tip and/or end of distal portion 13 of a catheter. In some examples, sensing electrodes may include mini-electrodes as described herein.

Additionally or alternatively, the model may also relate to the distance in space between a current-carrying electrode and one or more sensing electrodes. The current-carrying electrode may take a variety of forms. For example, the current-carrying electrode may be a distal ablation tip electrode 24 as shown in FIG. 1. Additionally or alternatively, the current-carrying electrode may include mini-electrodes and/or ring electrodes as described above with reference to FIGS. 1 and 2.

In some configurations, the potential measurement between a sensing electrode and a reference electrode may be modeled as being inversely proportional to the distance between a current-carrying electrode and a sensing electrode. For example, the relationship may be modeled as:

$$\varphi_{SEi} = \frac{K}{\|r_{CCE1} - r_{SEi}\|} + C$$

In this example, the parameter K may be used to assess tissue contact. The above equation is just an example. Other models and parameters are contemplated.

As stated above, the model may relate to both the potential differences between one or more sensing electrodes and the distance between a current-carrying electrode and sensing electrodes. For example, FIG. 4 illustrates an example distal end portion 213 including a current-carrying electrode 224 and four sensing electrodes 226, 234, 236 and 222. FIG. 4 also shows lead wires 232a-232e. It can be appreciated that the sensing electrodes 226, 234 and 236 may include mini-electrodes while the current-carrying electrode 224 may include a distal ablation tip electrode. Sensing electrodes 226, 234 and 236 may be disposed on distal tip ablation electrode 224. Further, a fourth sensing electrode 222 may be positioned proximate electrodes 224, 226, 234 and 236. Referring to FIG. 4, potential measuring electrode 222 may be a ring electrode. FIG. 4 is just an example. Combinations and configurations of a variety of electrode types may be utilized as either the sensing and/or current-carrying electrodes.

In some instances, the relationship between the above electrodes and potential values may be represented by the following equation:

$$\begin{bmatrix} \varphi_{SE1} \\ \varphi_{SE2} \\ \varphi_{SE3} \\ \varphi_{SE4} \end{bmatrix} = \begin{bmatrix} \frac{1}{\|r_{CCE1} - r_{SE1}\|} & 1 \\ \frac{1}{\|r_{CCE1} - r_{SE2}\|} & 1 \\ \frac{1}{\|r_{CCE1} - r_{SE3}\|} & 1 \\ \frac{1}{\|r_{CCE1} - r_{SE4}\|} & 1 \end{bmatrix} [KC]$$

It can be appreciated that the variables $$\begin{bmatrix} \varphi_{SE1} \\ \varphi_{SE2} \\ \varphi_{SE3} \\ \varphi_{SE4} \end{bmatrix}$$

represent the measured potential difference between the four sensing electrodes and a reference electrode. Additionally, the potential differences may be determined by system 10. Further, it can be appreciated that $\|r_{CCE1} - r_{SE1}\|$, $\|r_{CCE1} - r_{SE2}\|$, $\|r_{CCE1} - r_{SE3}\|$ and $\|r_{CCE1} - r_{SE4}\|$ represent the absolute value of the distance (in space) between the current-carrying electrode and the four sensing electrodes, respectively. It is further understood that these distances may be determined as the position (and distance) for every sensing electrode in relation to the current-carrying electrode is known.

The parameters K and C in the above system of linear equations can be estimated using a number of well-known techniques for optimization or linear regression. For example, least squares can be used to estimate K and C. Other methods are contemplated.

Scaling factor K may be inversely proportional to the conductivity of a given medium. In other words, the scaling factor K will be different for two mediums having different conductivities. For example, the conductivity of blood is greater than that of cardiac tissue, and therefore, the scaling factor K will be lower for blood as compared to cardiac tissue.

Knowing the potential differences and absolute distance values, it may be possible to solve the linear equation set (above) for the scaling factor, K. Is should be noted that in order to solve the disclosed linear equation set, sensing electrodes must be located at different distances away from the current injecting electrode. If, for example, the distances were all identical, then the matrix on the right-hand side of the equation would be singular and result in an infinite number of equally valid solutions. Referring to FIG. 4, it can be seen that sensing electrodes 226, 234, 236 and 222 are located at different distances from current injecting electrode 224.

FIG. 4 illustrates the sensing electrodes 226, 234, 236 and 222 positioned longitudinally along the catheter shaft 12. However, it is contemplated that the sensing electrodes 226, 234, 236 and 222 may be positioned in a configuration other than along the longitudinal axis and yet still maintain variable distances between the sensing electrodes and the current-carrying electrode. Additionally, in some instances it may be possible to reduce the number of sensing electrodes to two or three and solve the corresponding linear equation set for scaling factor K. In other instances, it may be desirable to increase the number of sensing electrodes; the parameter K can still be estimated using well-known techniques such as least squares.

It can be appreciated from the above discussion that it may be possible to utilize known variables to solve the disclosed linear equation for the scaling factor K. Therefore, system 10 may determine and compare different scaling factor values as the distal end portion 13 of catheter 12 is moved between different mediums (e.g. blood, tissue).

FIGS. 5a-5c illustrates distal end portion 213 positioned within a variety of mediums. For example, FIG. 5a shows distal end portion 213 surround entirely by blood. FIG. 5ab shows distal end portion 213 positioned at a blood/tissue interface. FIG. 5c shows distal end portion 213 partially embedded within tissue. As stated, the generated scaling factor K corresponding to FIGS. 5a-5c may be different for each different medium. The difference in the scaling factors may be utilized as a diagnostic indicator of the proximity of distal end portion 213 to tissue.

The following documents are herein incorporated by reference: U.S. Patent Application Pub. US2008/0243214, U.S. Patent Application Pub. US2014/0058375, U.S. Patent Application Pub. US2013/0190747, U.S. Patent Application Pub. US2013/0060245, and U.S. Patent Application Pub. US2009/0171345.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for diagnosing and/or treating a condition of the heart, the method comprising:
    advancing an electrophysiology catheter through a blood vessel to a position adjacent a target site, wherein the catheter comprises:
        a distal end portion;
        at least one current-carrying electrode disposed on the distal end portion; and
        a sensing assembly disposed on the distal end portion, wherein a first sensing electrode of the sensing assembly is spaced apart from the at least one current-carrying electrode by a first distance, wherein a second sensing electrode of the sensing assembly is spaced apart from the at least one current-carrying electrode by a second distance, wherein the first distance is different than the second distance;
    determining a scaling factor based upon the first distance and the second distance; and
    determining a conductivity of the target site based upon the scaling factor.

2. The method of claim 1, wherein the sensing assembly comprises four terminals.

3. The method of claim 1, wherein the at least one current-carrying electrode comprises at least one mini-electrode.

4. The method of claim 1, wherein the sensing assembly comprises one mini-electrode.

5. The method of claim 1, wherein the at least one current-carrying electrode comprises an ablation electrode and wherein the sensing assembly comprises an electrode disposed on the ablation electrode.

6. The method of claim 1, wherein the sensing assembly further comprises an electrode configured for both sensing and ablation and wherein the at least one current-carrying electrode comprises an electrode disposed on the ablation electrode.

7. The method of claim 1, wherein the at least one current-carrying electrode, the sensing assembly, or the at least one current-carrying electrode and the sensing assembly comprise a ring electrode.

8. The method of claim 1, wherein the at least one current-carrying electrode comprises an ablation electrode and a ring electrode, and wherein the sensing assembly comprises at least one mini-electrode.

9. The method of claim 1, wherein the at least one current-carrying electrode comprises at least one mini-electrode, and wherein the sensing assembly further comprises an electrode configured for both sensing and ablation and a ring electrode.

10. The method of claim 1, wherein the at least one current-carrying electrode comprises an ablation electrode and a mini-electrode and wherein the sensing assembly comprises a ring electrode and a mini-electrode.

11. An electrophysiology medical device, comprising:
    a distal end portion;
    at least one current-carrying electrode disposed on the distal end portion;
    a sensing assembly, disposed on the distal end portion, wherein a first sensing electrode of the sensing assembly is spaced apart from the at least one current-carrying electrode by a first distance, wherein a second sensing electrode of the sensing assembly is spaced apart from the at least one current-carrying electrode by a second distance, wherein the first distance is different than the second distance; and
    a controller configured to:
        determine a scaling factor based upon the first distance and the second distance; and
        determine a conductivity of the target site based upon the scaling factor.

12. The medical device of claim 11, wherein the sensing assembly comprises four terminals.

13. The medical device of claim 11, wherein the at least one current-carrying electrode comprises at least one mini-electrode.

14. The medical device of claim 11, wherein the sensing assembly comprises one mini-electrode.

15. The medical device of claim 11, wherein the at least one current-carrying electrode comprises an ablation electrode and wherein the sensing assembly comprises an electrode disposed on the ablation electrode.

16. The medical device of claim 11, wherein the sensing assembly further comprises an electrode configured for both sensing and ablation and wherein the at least one current-carrying electrode comprises an electrode disposed on the ablation electrode.

17. The medical device of claim 11, wherein the at least one current-carrying electrode, the sensing assembly, or the at least one current-carrying electrode and the sensing assembly comprise a ring electrode.

18. The medical device of claim 11, wherein the at least one current-carrying electrode comprises an ablation electrode and a ring electrode, and wherein the sensing assembly comprises at least one mini-electrode.

19. The medical device of claim 11, wherein the at least one current-carrying electrode comprises at least one mini-electrode, and wherein the sensing assembly further comprises an electrode configured for both sensing and ablation and a ring electrode.

20. The medical device of claim 11, wherein the at least one current-carrying electrode comprises an ablation electrode and a mini-electrode and wherein the sensing assembly comprises a ring electrode and a mini-electrode.

* * * * *